(12) United States Patent
Paul et al.

(10) Patent No.: US 7,695,603 B2
(45) Date of Patent: Apr. 13, 2010

(54) ELECTROOSMOTIC FLOW CONTROLLER

(75) Inventors: Phillip H. Paul, Livermore, CA (US); Don Wesley Arnold, Livermore, CA (US); Christopher G. Bailey, Pleasanton, CA (US)

(73) Assignee: Eksigent Technologies, LLC, Dublin, CA (US)

( * ) Notice: Subject to any disclaimer, the term of this patent is extended or adjusted under 35 U.S.C. 154(b) by 1194 days.

(21) Appl. No.: 11/200,369

(22) Filed: Aug. 8, 2005

(65) Prior Publication Data

US 2007/0000784 A1 Jan. 4, 2007

Related U.S. Application Data

(62) Division of application No. 09/942,884, filed on Aug. 29, 2001, now abandoned.

(60) Provisional application No. 60/298,147, filed on Jun. 13, 2001.

(51) Int. Cl.
*G05D 7/06* (2006.01)

(52) U.S. Cl. ...................... 204/600; 204/450

(58) Field of Classification Search ......... 204/450–455, 204/461, 600–605; 222/594, 595; 137/2, 137/7, 12, 115.03
See application file for complete search history.

(56) References Cited

U.S. PATENT DOCUMENTS

| | | | |
|---|---|---|---|
| 2,615,940 A | 10/1952 | Williams | 171/330 |
| 2,644,900 A | 7/1953 | Hardway, Jr. | 310/2 |
| 2,644,902 A | 7/1953 | Hardway, Jr. | 310/2 |
| 2,661,430 A | 12/1953 | Hardway, Jr. | 310/2 |
| 2,995,714 A | 8/1961 | Hannah | 331/107 |
| 3,143,691 A | 8/1964 | Hurd | 317/231 |
| 3,209,255 A | 9/1965 | Estes et al. | 324/94 |
| 3,427,978 A | 2/1969 | Hanneman et al | 103/1 |
| 3,544,237 A | 12/1970 | Walz | 417/48 |
| 3,682,239 A | 8/1972 | Abu-Romia | 165/1 |
| 3,921,041 A | 11/1975 | Stockman | |

(Continued)

FOREIGN PATENT DOCUMENTS

CN 2286429 Y 7/1998

(Continued)

OTHER PUBLICATIONS

Adamson, A.W. et al., "Electrical Aspects of Surface Chemistry," *Physical Chemistry of Surfaces*, pp. 185-187 (Wiley, NY 1997).

(Continued)

*Primary Examiner*—Nam X Nguyen
*Assistant Examiner*—Gurpreet Kaur
(74) *Attorney, Agent, or Firm*—Sheldon Mak Rose & Anderson PC; Laura M. Lloyd

(57) ABSTRACT

Electroosmotic flow controllers and methods of fluid flow control are described. The invention uses an electroosmotically generated flow component in conjunction with a pressure driven flow component to modulate fluid flow. The devices and methods of the invention may include salt bridges for making electrical connection between a power supply and a channel filled with a porous dielectric material and a fluid. Embodiments including flow controllers and flow splitters are described as is their use in a variety of fluid handling applications.

16 Claims, 11 Drawing Sheets

U.S. PATENT DOCUMENTS

| | | | |
|---|---|---|---|
| 3,923,426 A | 12/1975 | Theeuwes | |
| 4,347,131 A | 8/1982 | Brownlee | 210/101 |
| 4,638,444 A | 1/1987 | Laragione et al. | 364/510 |
| 4,681,678 A | 7/1987 | Leaseburge et al. | 210/101 |
| 4,684,465 A | 8/1987 | Leaseburge et al. | 210/198.2 |
| 4,767,279 A | 8/1988 | Dourdeville et al. | 417/18 |
| 4,810,392 A | 3/1989 | Fulton et al. | 210/659 |
| 4,921,041 A | 5/1990 | Akachi | 165/104.29 |
| 5,032,264 A | 7/1991 | Geiger | |
| 5,040,126 A | 8/1991 | Allington | 364/510 |
| 5,219,020 A | 6/1993 | Akachi | 165/104.26 |
| 5,249,929 A | 10/1993 | Miller et al. | 417/207 |
| 5,302,264 A * | 4/1994 | Welch et al. | 204/450 |
| 5,312,233 A | 5/1994 | Tanny et al. | 417/316 |
| 5,418,079 A | 5/1995 | Diethelm | 429/26 |
| 5,429,728 A | 7/1995 | Gordon | |
| RE35,010 E | 8/1995 | Price | 222/1 |
| 5,482,608 A | 1/1996 | Keely et al. | |
| 5,573,651 A | 11/1996 | Dasgupta et al. | 204/601 |
| 5,630,706 A | 5/1997 | Yang | 417/3 |
| 5,664,938 A | 9/1997 | Yang | 417/313 |
| 5,670,707 A | 9/1997 | Fennell et al. | 73/1 |
| 5,777,213 A | 7/1998 | Tsukazaki et al. | 73/61.52 |
| 5,797,719 A | 8/1998 | James et al. | 417/46 |
| 5,814,742 A | 9/1998 | Vissers et al. | 73/863.73 |
| 5,858,193 A | 1/1999 | Zanzucchi et al. | 204/601 |
| 5,888,050 A | 3/1999 | Fitzgerald | 417/46 |
| 5,915,401 A | 6/1999 | Menard et al. | 137/12 |
| 5,942,093 A | 8/1999 | Rakestraw et al. | 204/450 |
| 5,961,800 A | 10/1999 | McBride et al. | 204/450 |
| 5,997,746 A | 12/1999 | Valaskovic | |
| 6,004,443 A | 12/1999 | Rhodes et al. | |
| 6,012,902 A | 1/2000 | Parce | 417/48 |
| 6,013,164 A | 1/2000 | Paul et al. | |
| 6,019,882 A * | 2/2000 | Paul et al. | 204/450 |
| 6,045,933 A | 4/2000 | Okamoto | 429/17 |
| 6,068,243 A | 5/2000 | Hoggan | 256/34 |
| 6,068,767 A | 5/2000 | Garguilo et al. | 210/198.2 |
| 6,086,243 A | 7/2000 | Paul et al. | 366/273 |
| 6,106,685 A | 8/2000 | McBride et al. | 204/600 |
| 6,139,734 A | 10/2000 | Settlage et al. | 210/198.2 |
| 6,149,787 A * | 11/2000 | Chow et al. | 204/451 |
| 6,167,910 B1 | 1/2001 | Chow | |
| 6,221,332 B1 | 4/2001 | Thumm et al. | |
| 6,224,728 B1 | 5/2001 | Oborny et al. | 204/450 |
| 6,255,551 B1 | 7/2001 | Shapiro et al. | 588/204 |
| 6,277,257 B1 | 8/2001 | Paul et al. | 204/450 |
| 6,280,967 B1 | 8/2001 | Ransom et al. | 435/29 |
| 6,287,440 B1 | 9/2001 | Arnold et al. | 204/450 |
| 6,289,914 B1 | 9/2001 | Tommasi | 137/15.18 |
| 6,290,909 B1 | 9/2001 | Paul et al. | 422/70 |
| 6,299,767 B1 | 10/2001 | Dourdeville | 210/198.2 |
| 6,315,905 B1 | 11/2001 | Settlage et al. | 210/656 |
| 6,319,410 B1 | 11/2001 | Allington et al. | 210/634 |
| 6,386,050 B1 | 5/2002 | Yin et al. | 73/861.95 |
| 6,402,946 B1 | 6/2002 | Spraul et al. | 210/198.2 |
| 6,404,193 B1 | 6/2002 | Dourdeville | 324/306 |
| 6,406,605 B1 | 6/2002 | Moles | 204/601 |
| 6,416,642 B1 | 7/2002 | Alajoki et al. | |
| 6,428,666 B1 | 8/2002 | Singh et al. | |
| 6,460,420 B1 | 10/2002 | Paul et al. | 73/861.52 |
| 6,477,410 B1 | 11/2002 | Henley et al. | 604/20 |
| 6,616,823 B2 | 9/2003 | Kopf-Sill | |
| 6,619,311 B2 | 9/2003 | O'Connor et al. | |
| 6,719,535 B2 | 4/2004 | Rakestraw et al. | 417/50 |
| 6,766,817 B2 | 7/2004 | da Silva | |
| 2001/0008212 A1 | 7/2001 | Shepodd et al. | 204/451 |
| 2002/0017484 A1 | 2/2002 | Dourdeville | 210/198.2 |
| 2002/0022802 A1 | 2/2002 | Simpson | 604/186 |
| 2002/0070116 A1 | 6/2002 | Ohkawa | 204/603 |
| 2002/0072126 A1 | 6/2002 | Chervet et al. | 436/161 |
| 2002/0076598 A1 | 6/2002 | Bostaph et al. | 429/38 |
| 2002/0125134 A1 | 9/2002 | Santiago et al. | 204/450 |
| 2002/0189947 A1 | 12/2002 | Paul et al. | |
| 2002/0195344 A1 | 12/2002 | Neyer et al. | |
| 2003/0052007 A1 | 3/2003 | Paul et al. | |
| 2003/0138678 A1 | 7/2003 | Preidel | 429/13 |
| 2003/0190514 A1 | 10/2003 | Okada et al. | 429/31 |
| 2003/0215686 A1 | 11/2003 | DeFilippis et al. | 429/34 |
| 2004/0011648 A1 | 1/2004 | Paul et al. | 204/450 |
| 2004/0107996 A1 | 6/2004 | Crocker et al. | |

FOREIGN PATENT DOCUMENTS

| | | |
|---|---|---|
| DE | 196 25 648 | 1/1997 |
| EP | 0183950 | 6/1986 |
| GB | 2 303 885 | 3/1997 |
| JP | S50-116893 | 9/1975 |
| JP | 6197567 | 5/1986 |
| JP | 61237717 | 10/1986 |
| JP | H1-68503 | 5/1989 |
| JP | 618964 | 3/1994 |
| JP | H7-072934 | 3/1995 |
| JP | 09281077 | 10/1997 |
| WO | 8502225 | 5/1985 |
| WO | WO 96/39252 | 12/1996 |
| WO | WO99/16162 | 9/1998 |
| WO | WO 99/67639 | 12/1999 |
| WO | WO 00/04832 | 2/2000 |
| WO | WO00/16937 | 3/2000 |
| WO | WO 00/43766 | 7/2000 |
| WO | WO00/55502 | 9/2000 |
| WO | WO 00/65337 | 11/2000 |
| WO | WO00/79131 | 12/2000 |
| WO | WO 02/068821 | 9/2002 |
| WO | WO 2004/007080 | 1/2004 |

OTHER PUBLICATIONS

Carvalho, R.T. et al. "Slow-flow measurements and fluid dynamics analysis using the Fresnel drag effect," *Applied Optics*, vol. 33, No. 25 (Sep. 1, 1994).

Davis, M.T. et al., "Low Flow High-Performance Liquid Chromatography Solvent Delivery System Designed for Tandem Capillary Liquid Chromatography—Mass Spectrometry," *Am. Soc. for Mass Spectrometry*, 6:571-577 (1995).

Davis, M.T. et al., "Variable Flow Liquid Chromatography-Tandem Mass Spectrometry and the Comprehensive Analysis of Complex Protein Digest Mixtures," *Am. Soc. For Mass Spectrometry*, 8:1059-1069 (1997).

Desiderio at al., "A new electrode chamber for stable performance in capillary electrophoresis," *Electrophoresis*, 20:525-528 (1999).

Enoksson, Peter et al., "A Silicon Resonant Sensor Structure for Coriolis Mass-Flow Measurements," *Journal of Microelectromechanical Systems*, vol. 6, No. 2 (Jun. 1997).

Gan, W. et al. "Mechanism of porous core electroosmotic pump flow injection system and its application to determination of chromium(VI) in waste-water," *Talanta* 51:667-675 (2000).

Kobatake, Y. et al., "Flows Through Charged Membranes. I. Flip-Flop Current vs Voltage Relation," *J. Chem. Phys.* 40(8):2212-2218 (Apr. 1964).

Kobatake, Y. et al., "Flows Through Charged Membranes. II. Oscillation Phenomena," *J. Chem. Phys.* 40(8):2219-2222 ( Apr. 1964).

Langridge, J. et al., "Nano-Scale Variable Flow Chromatography For High Sensitivity Proteome Studies," Presented at COMBIO, Canberra, Australia, Sep. 30-Oct. 4, 2001, 4 pages.

Langridge, J. et al., "High Sensitivity Phosphoprotein Analysis Using a Combination of Variable Flow Chromatography and Precursor Ion Discovery on a Qtof Mass Spectrometer," Presented at 19th Montreux Symposium, Montreux, Switzerland, Nov. 6-8, 2002, 4 pages.

LeBlanc, Jacques C., "The Stableflow Pump—a low-noise and drift-free pump for high performance liquid chromatography," *Rev. Sci. Instrum.* 62(6), 1642-1646 (Jun. 1991).

Martin, S.E. et al., "Subfemtomole MS and MS/MS Peptide Sequence Analysis Using Nano-HPLC Micro-ESI Fourier Transform Ion Cyclotron Resonance Mass Spectrometry," *Analytical Chemistry*, 72(18):4266-4274 (2000).

McNair, H.M., "High Pressure Liquid Chromatography Equipment—II," *Journal of Chromatographic Science* (Aug. 1974).

Morrison, F.A. et al., "Electrokinetic Energy Conversion in Ultrafine Capillaries," *J. Chem. Phys.* 43:2111-2115 (1965).

Paul, P.H. et al., "Electrokinetic Generation Of High Pressures Using Porous Microstructures," *Micro Total Analysis Systems*, pp. 49-52 (1998).

Paul, P.H. et al., "Electrokinetic Pump Application in Micro-Total Analysis Systems Mechanical Actuation to HPLC," *Micro Total Analysis Systems*, pp. 583-590 (2000).

Rastogi, R.P., "Irreversible Thermodynamics of Electro-osmotic Effects," *J. Scient. Ind. Res.*, (28):284-292 (Aug. 1969).

Schmid, G., "Electrochemistry of capillary systems with narrow pores. II. Electroosmosis," *J. Membrane Sci.* 150:159-170 (1998).

Schmid, G. et al., "Electrochemistry of capillary systems with narrow pores V. Streaming potential: Donnan hindrance of electrolyte transport," *J. Membrane Sci.* 150:197-209 (1998).

Stahl, D.C., "Data-Controlled Automation of Liquid Chromatography/Tandem Mass Spectrometry Analysis of Peptide Mixtures," *Am. Soc. For Mass Spectromtry*, 7:532-540 (1996).

Vissers, Johannes P.C., "Recent developments in microcolumn liquid chromatography," *Journal of Chromatography A*, 856, 117-143 (1999).

Vissers, J.P.C. et al., "A Novel Interface for Variable Flow Nanoscale LC/MS/MS for Improved Proteome Coverage," *Am. Soc. for Mass Spectrometry*, 13:760-771 (2002).

Zeng, S. et al., "Fabrication and characterization of electroosmotic micropumps," *Sensors and Actuators*, B 79:107-114 (2001).

Agilent Technologies: Agilent 1100 Series Capillary LC System, A one-vendor solution for highest sensitivity and robustness, 7 pages.

Office Action for U.S. Appl. No. 09/942,884 mailed on Apr. 22, 2004, 5 pages.

Office Action for U.S. Appl. No. 09/942,884 mailed on Aug. 12, 2004, 9 pages.

Office Action for U.S. Appl. No. 09/942,884 mailed on Mar. 9, 2005, 7 pages.

Advisory Action for U.S. Appl. No. 09/942,884, mailed on May 24, 2005, 3 pages.

Office Action for U.S. Appl. No. 10/155,474 mailed on Jul. 13, 2005, 5 pages.

Office Action for U.S. Appl. No. 10/155,474 mailed on Nov. 4, 2005, 6 pages.

Office Action for U.S. Appl.. No. 10/155,474 mailed on Jul. 18, 2006, 6 pages.

International Search Report for PCT App. No. PCT/US02/19121, mailed Jan. 3, 2003, 4 pages.

International Preliminary Examination Report for PCT App. No. PCT/US02/19121, mailed Mar. 7, 2003, 4 pages.

Office Action for U.S. Appl. No. 10/480,619, mailed Oct. 9, 2007, 6 pages.

Office Action for U.S. Appl. 10/246,284, mailed Sep. 30, 2005, 6 pages.

Office Action for U.S. Appl. 10/246,284, mailed Jan. 27, 2006, 6 pages.

Office Action for U.S. Appl. No. 10/246,284, mailed Oct. 4, 2006, 5 pages.

Office Action for U.S. Appl. 10/246,284, mailed Jul. 16, 2007, 6 pages.

International Search Report, for PCT Application No. PCT/US03/30008, mailed Mar. 4, 2004, 4 pages.

Notice of Rejection for Japanese Patent Application No. 2003-504171, dated May 7, 2008, 3 pages (unofficial English translation).

European Search Report, EP 02 73 9909.

Ananthakrishnan, V. et al., "Laminar Dispersion in Capillaries: Part I. Mathematical Analysis," *A.I.Ch.E. Journal*, 11(6):1063-1072 (Nov. 1965).

Aris, R, "On the dispersion of a solute in a fluid flowing through a tube," Oxidation of organic sulphides. VI, *Proc. Rov. Soc. (London)*, 235A:67-77.

Burgreen, D. et al., "Electrokinetic Flow in Ultrafine Capillary Slits," *The Journal of Physical Chemistry*, 68:(5) 1084-1091.

Chatwin, P.C. et al., "The effect of aspect ratio on longitudinal diffusivity in rectangular channels," *J. Fluid Mech.*, 120:347-358 (1982).

Doshl, Mahendra R. et al., "Three Dimensional Laminar Dispersion in Open and Closed Rectangular Conduits," *Chemical Engineering Science*, 33:795-804 (1978).

Drott, J. et al., "Porous silicon as the carrier matrix in microstructured enzyme reactors yielding high enzyme activities," *J. Micromech. Microeng.* 7:14-23 (1997).

Jessensky O. et al., "Self-Organized Formation of Hexagonal Pore Structures in Anodic Alumina," *J. Electrochem. Soc.* 145(11):3755-374 (Nov. 1998).

Johnson, David Linton et al., "New Pore-Size Parameter Characterizing Transport in Porous Media," *Physical Review Letters*, 57(20):2564-2567 (Nov. 17, 1986)

Johnson, David Linton et al., "Theory dynamice permeability and tortuousity in fluid-saturated porous media," *J. Fluid Mech.* 176:379-402 (1987).

Johnson, David Linton et al., "Dependence of the conductivity of a porous medium on electrolyte conductivity," *Physical Review Letters*, 37(7):3502-3510 (Mar. 1, 1998).

Ma, Ying et al., "A review of zeolite-like porous materials," *Microporous and Mesoporous Materials*, 37:243-252 (2000).

Nakanishi, Kazuki et al., "Phase separation in silica sol-gel system containing polyacrylic acid, I. Gel formation behavior and effect of solvent composition," *Journal of Crystalline Solids*, 139:1-13 (1992).

Peters, Eric C. et al., "Molded Rigid Polymer Monoliths as Separation Media for Capillary Electrochromatography," *Anal. Chem.*, 69:3646-3649 (1997).

Philipse, Albert P., "Solid opaline packings of colloidal sillica spheres," *Journal of Materials Science Letters*, 8:1371-1373 (1989).

Rice, C. L. et al., "Electrokinetic Flow in a Narrow Cylindrical Capillary," *The Journal of Physical Chemistry*, 69(11):4017-4023 (Nov. 1966).

Rosen, Milton J., "2. Adsorption of Surface-Active Agents at Interfaces: The Electrical Double Sons Layer," *Surfactants and Interfacial Phenomena*, Second Ed., John Wiley & Sons.

Taylor, Geoffrey, "Dispersion of soluble matter in solvent flowing slowly through a tube," *Proc. Roy. Soc. (London)* 21:186-203.

Weston, Andrea et al., "Chapter 3 Instrumentation for High-Performance Liquid Chromatography," *HPLC and CE, Principles and Practice*, pp. 82-85, Academic Press.

Wijnhoven, Judith et al., "Preparation of Photonic Crystals Made of Air Spheres in Titania," *Science*, 281:802-804(Aug. 7, 1998).

Yazawa, T.,"Present Status and Future Potential of Preparation of Porous Glass and its Application," *Key Engineering Materials*, 115:125-146 (1995).

Notice of Rejection for Japanese Patent Application No. 2004-538456, dated May 26, 2009, 3 pages.

\* cited by examiner

ELECTROOSMOTIC FLOW CONTROLLER

CROSS-REFERENCE TO RELATED APPLICATIONS

This application is a divisional of U.S. patent application Ser. No. 09/942,884, filed on Aug. 29, 2001, now abandoned which claims the benefit of U.S. Provisional Patent Application 60/298,147, filed Jun. 13, 2001, the entire contents of which are hereby incorporated herein by reference in their entirety.

BACKGROUND OF THE INVENTION

The invention pertains to the fields of fluid handling and electroosmosis. More particularly, the invention pertains to electroosmotic flow controllers.

Flow controllers are used to manage the flow of fluids through conduits. Traditionally, control of fluid volume and or fluid composition by flow controllers is accomplished by combinations of pumps and valves. In some applications, flow controllers are used to control fluid flows on the order of many milliliters or more per minute, while in other applications, the fluid flow rates are orders of magnitude smaller. Prior art flow controllers tend to suffer from a variety of shortcomings. In high flow and in low flow applications, prior art flow controllers have difficulty in maintaining precise flow rates in the face of changing head pressures, such as those generated by pumping devices. In addition, mechanical feedback loops used to control flow rates through flow controllers often introduce additional imprecision and dead space into flow-controlled devices.

Microfluidic systems are playing an increasingly important role in developing advanced separation techniques needed for chemical analysis. Currently, chemical separations and purification represent severe bottlenecks in many biotechnology and drug discovery applications. Traditional scale separation systems are not compatible with the speed and small sample sizes typically required for high throughput analytical techniques. Analogous to transistors on a computer chip, microfluidic separation systems can be easily fabricated and run in multiple parallel arrays. The increased throughput and speed attained will be critical to allow separation technology to keep pace with the explosive growth of biotechnological advancement.

The recently completed sequencing of the human genome has tremendously increased our knowledge of the role genes play in disease. Translating this knowledge into improved medical diagnostics and treatments requires a much more thorough understanding of biological processes at the cellular and molecular levels. One promising approach for developing the necessary understanding involves analyzing the expression of cellular proteins in normal and disease states. Another approach involves generating protein-protein interaction maps that characterize binding interactions among different proteins to better understand the diverse biochemical signaling pathways underlying normal and pathological cell physiology.

These analytical tasks are in many respects more challenging than genome sequencing efforts. In contrast to DNA, which is chemically and structurally similar irrespective of nucleic acid sequence, proteins have enormous chemical diversity. Thus, different proteins may have different molecular weights, different electronic charges, different solubilities, etc. depending upon their amino acid composition and post-translational modifications.

Therefore, the reliable microseparation techniques developed for gene sequencing are inadequate for protein analysis. Moreover, the genome is a static entity. It does not significantly change over time and identical sequences of DNA are found in almost all of the cells in the body. In contrast, the complement of expressed proteins (i.e., the "proteome") in, for example, a red blood cell, is very different than that expressed, e.g., in a neuron, or a skin cell, or a liver cell. Also, the proteome changes as a function of age and disease state. Further, considering alternative splicing possibilities, it has been estimated that there are 100 times more proteins present than the number of genes. Given this formidable task, it is clear that fast, reproducible and robust separation methods are needed to thoroughly characterize protein expression levels and interactions.

Currently, cell protein extracts are most often analyzed using 2 dimensional gel ("2D gel") electrophoretic techniques, followed by one or more rounds of mass spectrometry ("MS"). Many problems exist with 2D gels, however. Inter- and intra-laboratory reproducibility is notoriously poor. The analysis is time consuming, the 2D separation typically taking 1-2 days. After this, proteins on the gel must be stained, identified, cut out, extracted from the gel matrix, destained and serially loaded into a mass spectrometer. A complete analysis for a single cell can take months or longer.

An alternative analytical approach involves the use of gradient liquid chromatography ("LC") followed by MS. While this technique does not have the separation capacity of 2D gel electrophoresis, it is faster and more reproducible. The proteins found in the effluent of the separation column can be fed directly into a mass spectrometer. Commercially available high performance liquid chromatography ("HPLC") systems for carrying out analytical separations often use separation columns having diameters on the order of 2-5 millimeters and run at flow rates of a few milliliters per minute ("ml/min"). Since the flow rate into the MS is on the scale of microliters per minute ("µl/min") or less, most of the effluent from the HPLC, including that containing possibly valuable sample, is thrown away. Using a typical HPLC unit, these tandem liquid chromatography/mass spectroscopy ("LC/MS") analyses take about an hour.

Increasing the throughput of HPLC separations can be accomplished in several ways. For example, separations can be carried out more quickly and multiple systems can be run in parallel. Given the high cost and large size of conventional HPLC systems, it is impractical to run more than a few systems in parallel. Also, the speed at which a separation can be done is limited by the large sample requirements of the system.

Microscale HPLC systems can, in theory, address both of these needs. Moreover, microscale systems offer other advantages such as reduced waste generation and low sample volume requirements. However, most currently available micro HPLC systems are simply large scale systems outfitted with flow reducers and dampers, and as such are not truly microscale flow devices. The macroscale high pressure pumps used in these systems are often unable to meter fluid flow with sufficient accuracy to generate reliable and rapid gradients, which are critical to reproducible HPLC analysis.

The present invention addresses these and other shortcomings of the prior art by providing electroosmotic flow controllers capable of providing precise flow rates in high and low flow applications using a combination of pressure-driven and electroosmotically-driven flows.

SUMMARY OF THE INVENTION

The present invention provides an electroosmotic flow controller capable of controlling fluid flow through a combination of electroosmotic and pressure-driven flows. The inventors have recognized that by adding an electroosmotic flow component to a pressure-driven flow component, one may effect rapid and accurate flow control over a wide range of flow rates. Devices embodying the invention may be made with few or no moving parts and are compatible with most solvents. They may be readily fabricated as true microscale devices. Devices embodying the present invention may be used to reliably and accurately correct for over pressurizations, pressure waves, and flow inaccuracies caused by the use of oversized pumps in microseparations. The devices can be driven by virtually any type of pressure generator, including high pressure syringe pumps, hand pumps, or air-driven systems.

Thus, in one aspect, the invention includes a flow controller that comprises a channel having a fluid inlet in liquid communication with a fluid source at pressure P1, a fluid outlet at pressure P2, wherein P2<P1, and a porous dielectric material disposed in the channel, a fluid contained within the channel, spaced electrodes in electrical communication with the fluid, a power supply in electrical communication with the electrodes for applying an electric potential to the spaced electrodes, whereby the electric potential generates an electroosmotically-driven flow component through the channel that modulates a pressure-driven flow component resulting from the P1–P2 pressure differential.

In another preferred embodiment, the flow controller further comprises in addition to the elements set forth above, a first flow element having a first flow element inlet in liquid communication at a first node at pressure PN with the fluid inlet and the fluid source, and a first flow element outlet at pressure P3, and the electroosmotically driven flow affects the proportion of fluid flowing through the channel and the first flow element.

In another preferred embodiment, the flow controller further comprises in addition to the elements set forth above, a second flow element having a second flow element inlet in liquid communication at the fluid source at pressure P1 with the fluid inlet and the fluid source, and a second flow element outlet in liquid communication at the node at pressure PN, and the second flow element affects the amount of fluid available at the node for passage through the channel and the first flow element.

In another preferred embodiment, the flow controller includes at least one sensor for monitoring at least one control signal, and a feedback control mechanism operatively connected to the sensor and the power supply, wherein the feedback control mechanism maintains the control signal within a predetermined range by modulating the electric potential applied by the power supply.

In another preferred embodiment, the sensor is selected from the group consisting of a pressure transducer, a flowmeter, a temperature sensor, a heat flux sensor, a displacement sensor, a load cell, a strain gauge, a conductivity sensor, a selective ion sensor, a pH sensor, a flow spectrophotometer, and a turbidity sensor.

In another preferred embodiment, the feedback control mechanism is programmable.

In still another preferred embodiment, the flow controller further comprises a second channel having a second fluid inlet in liquid communication with a second fluid source at pressure P4, a second fluid outlet at pressure P5, wherein P5<P4, and a second porous dielectric material disposed within the second channel, a second fluid contained within the second channel, second spaced electrodes in electrical communication with the second fluid, a second power supply in electrical communication with the second electrodes for applying a second electric potential to the second spaced electrodes, so that the second electric potential generates a second electroosmotically-driven flow component through the second channel that modulates a second pressure-driven flow component resulting from the P4–P5 pressure differential, a second flow element having a second flow element inlet in liquid communication at a second node at pressure $PN_2$ with the second fluid inlet and the second fluid source, and a second flow element outlet in liquid communication at a third node with the first flow element outlet at pressure P3, so that the second electroosmotically driven flow affects the proportion of second fluid flowing through the second channel and the second flow element. One of ordinary skill will understand that the first and second power supplies need not be separate power supply units. In many instances it is preferable from a manufacturing economy standpoint that the first and second power supplies share components for generating power output. All that is intended by "second power supply" is a source of power output or potential difference that can be set independently from the first power supply. Thus, a single power supply unit with multiple, independently controllable voltage outputs would be considered a first and a second power supply according to the present invention.

In a further preferred embodiment, the flow controller further comprises a plurality of sensors that monitor a plurality of control signals and a feedback control mechanism operatively connected to the sensors, and to the power supplies so that the feedback control mechanism maintains the control signals within predetermined ranges by controlling the electric potentials applied by the power supplies.

In another preferred embodiment, the sensors are selected from the group consisting of a differential pressure transducer, a flowmeter, a temperature sensor, a heat flux sensor, a displacement sensor, a load cell, a strain gauge, a conductivity sensor, a selective ion sensor, a pH sensor, a flow spectrophotometer, and a turbidity sensor.

In a further preferred embodiment, the programmable feedback control mechanism maintains the sum of the fluid flowing through the first flow element outlet and the second flow element outlet within a predetermined range by monitoring a control signal originating at the third node, and adjusting the electric potentials applied by the power supplies.

In a preferred embodiment, the control signal originating at the third node is proportional to the pressure, P3.

In another preferred embodiment, the programmable feedback control mechanism maintains the relative amounts of fluid flowing from the first flow element outlet and the second flow element outlet within a predetermined range by monitoring control signals originating at the first node and the second node, and adjusting the electric potentials applied by the power supplies.

In yet another preferred embodiment, the control signals originating at the first node and the second node are proportional to the pressures PN and $PN_2$.

In a preferred embodiment, the fluid contained within the channel comprises electrolytes.

In yet another preferred embodiment, the power supply is a variable power supply.

In another preferred embodiment, the pressure-driven and electroosmotically-driven flows are in the same direction.

In another preferred embodiment, the pressure-driven and electroosmotically-driven flows are in opposite directions.

In another preferred embodiment, the electrical communication between the spaced electrodes and the channel fluid is accomplished through a bridge.

In one preferred embodiment, the channel has a circular cross-section. In another embodiment, the channel cross-section is other than circular.

In another preferred embodiment, the channel comprises a fused silica capillary.

In another preferred embodiment, the porous dielectric material includes silica particles.

In yet another preferred embodiment, the silica particles have a diameter of between about 100 nm and 5 μm.

In a further preferred embodiment, the porous dielectric material includes porous dielectric materials fabricated by processes selected from the group consisting of lithographic patterning and etching, direct injection molding, sol-gel processing, and electroforming.

In an additional preferred embodiment, the porous dielectric material includes organic polymer materials.

It is yet another objective of the invention to provide methods for controlling fluid flow. In a preferred embodiment, the method comprises applying an electric potential to spaced electrodes in communication with a fluid contained within a porous dielectric disposed within a channel, the channel having a fluid inlet in liquid communication with a fluid source at pressure P1, and a fluid outlet at pressure P2, wherein P2<P1 and whereby the electric potential generates an electroosmotically-driven flow component through the channel that modulates a pressure-driven flow component resulting from the P1–P2 pressure differential.

In another preferred embodiment, the flow control method comprises applying an electric potential to spaced electrodes in communication with a fluid contained within a porous dielectric disposed within a channel, the channel having a fluid inlet in liquid communication at a node at pressure PN with a fluid source at pressure P1 and a first flow element inlet, and a fluid outlet at pressure P2, wherein P2<P1 and whereby the electric potential generates an electroosmotically-driven flow component through the channel that affects the proportion of fluid flowing through the channel and the first flow element.

DETAILED DESCRIPTION OF PREFERRED EMBODIMENTS

Figure 1:
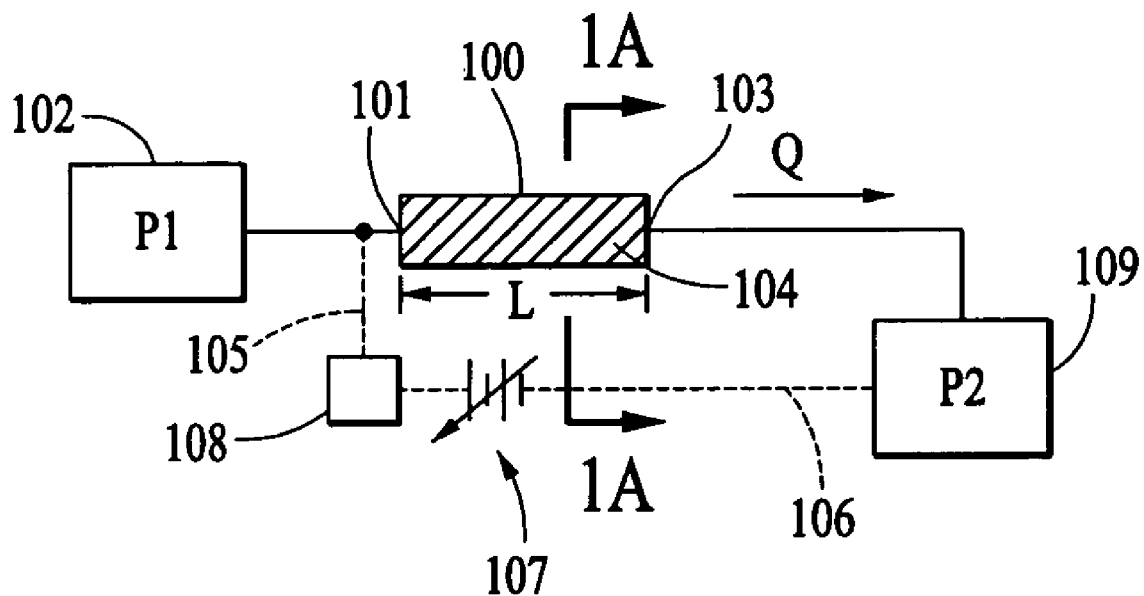
FIG. 1 illustrates an embodiment of the flow controller of the present invention.

Electroosmotic flow in open channels and in porous media is a well-know phenomena and has been the subject of many experimental and theoretical studies. When a liquid (e.g. water) is in contact with a dielectric solid (e.g. glass, silica, many plastics and ceramics) the natural electrochemistry of the interaction produces a thin layer of net charge density in the fluid that is localized to the liquid-solid interface. An electrical field applied so as to produce a component tangential to this interface will produce a Lorentz force on this net charge density. This net force will cause a motion of the net charge and this motion will be imparted by viscous action to the remaining neutral fluid. Thus in a channel packed with a porous dielectric material that is filled or saturated by an appropriate liquid, a potential difference $\Delta V$ applied end-to-end will produce what is known as an electroosmotic flow of the liquid. This electroosmotic flow may compete with or even dominate the flow that could be produced by application of a pressure difference across the same channel.

Electroosmotic flows may be generated using a wide variety of fluids and dielectric materials. The fluid should provide conditions that yield a high zeta potential with respect to the porous dielectric material. The fluid may be a pure fluid or a mixture of pure fluids that may have in addition some small concentration of a conducting species such as various ions. Preferably, the pure fluids should have high dielectric constant (between about 5 and 100 relative units), low dynamic viscosity (between about 0.1 and 2 centipoise) and low conductivity (between about $10^{-4}$ and $10^{-14}$ mho/m). Additives are preferably introduced to define or control the pH and ionic strength of the fluid. Additives should be of a kind and of a concentration to completely dissolve in the fluid. The kind and concentration of these additives preferably are chosen so as to enhance or optimize the zeta potential under the conditions imposed by the size of the pores in the porous dielectric medium.

Suitable pure fluids include by way of example, but not limitation: distilled and/or deionized water, cyclic carbonates, methanol, ethanol, 1-propanol, 2-propanol, 1-butanol, 1-pentanol, 1-hexanol, 1-heptanol, benzyl-alcohol, nitromethane, nitrobenzene, butanone, dimethoxymethane, dimethylacetamide, dioxane, p-dioxane, acetonitrile, formamide, tetrahydrofuran, dimethyl formamide, acetone, acetic acid, triethylamine, dichloromethane, ethylene glycol, dimethylsulfoxide, ammonium acetate.

The zeta potential may be thought of as a property of a fluid-solid interface. It is desirable that the magnitude of this zeta potential be in the range of about unity to 150 mV. The zeta potential may be either positive or negative in sign. It is known that the sign and magnitude of the zeta potential are dependent on the dielectric constant of the fluid, the pH of the fluid, on the ionic strength of the fluid and on the type of ions in the fluid. To yield a zeta potential, generally, the surface of the porous dielectric material exhibits acidic or basic sites that become ionized in the presence of the fluid. These ionizable surface sites may be native to the material or may be the result of adsorption of some species onto the surface material.

Native ionizable materials include by way of example, but not limitation: silica, which exhibits acidic surface sites, alumina (amphoteric) which can exhibit basic or acidic surface sites, Nylon (zwitterionic) which exhibits both acidic (carboxyl) and basic (amine) surface sites. The sign of the zeta potential is the same as the sign of the net surface charge.

As an example of adsorption leading to surface charge, consider admixtures of polyethylene or polypropylene with ionic surfactants. Polyethylene and polypropylene are non-polar polymers having no native ionizable sites. In an aqueous solution containing certain ionic surfactants (e.g. sodium dodecyl sulfate), the hydrophobic tail of the surfactant adsorbs to the polymer. The charged end of the surfactant then appears as a charge site on the surface.

The degree of ionization of the surface sites depends on the pH of the fluid. In most cases there is a pH at which the surface is net neutral and hence the zeta potential is zero. The zeta potential reaches a maximum value for pH values well-above (for acidic surface sites) or pH values well below (for basic surface sites) the pH value at which the surface is net neutral. Ionizable surface sites can be added to a material by chemical reaction or grafting, or induced by creation of reactive surface chemistry or creation of defects via plasma or radiation treatment.

The host dielectric material is selected for properties of: high zeta potential, sign of the zeta potential, insolubility and stability in the fluid with additives, low electrical conductivity, and sufficient mechanical strength.

Examples of suitable oxide materials include: silica, alumina, titania, zirconia, cerium oxide, lanthanum oxide, yttrium oxide, hafnium oxide, magnesium oxide, tantalum oxide. These oxides may be amorphous or glassy or crystalline and may be combined in mixtures having other minor oxide components.

Examples of suitable glass materials include: crown or float or boro-silicate glasses, lanthanum or flint or dense flint glasses, Pyrex™.

Examples of suitable nitride materials include: silicon nitride, boron nitride, aluminum nitride.

Examples of suitable polymers include: Nafion™ (Dupont Trade name, a sulfonated PTFE), polysulfone, polyethersulfone, cellulose acetate, mixed cellulose esters, polycarbonate, polyacrylonitrile, polyvinylidene fluoride, polyamide (Nylon), silicone elastomers, polymethacrylate, and nitro-cellulose (also called collodion).

Other classes of suitable materials include certain semiconductors, carbides (e.g. titanium carbide) and silicides (e.g. germanium silicide).

Ionic species in the fluid are termed counterions (ions that have a charge sign opposite the sign of the zeta potential) and coions (ions that have a charge sign the same as the sign of the zeta potential). It is the net excess of surface charge-balancing counterions near the surface/fluid interface that determines the zeta potential. Increasing the concentration of counterions in the bulk fluid tends to shield the surface charge and thus reduces the magnitude of the zeta potential. For example, consider silica as the dielectric material exposed to water at pH 7 as the pure fluid and KCl as an additive. The zeta potential for this system is measured to be negative with magnitudes of: 120 mV, 100 mV, 70 mV and 30 mV for KCl concentrations of 0.1, 1, 10 and 100 millimolar, respectively. The valence of the counterion may also have a pronounced effect on the character of the zeta potential. Polyvalent (i.e. multiply charged) counterions may bind to the surface sites thus changing the pH of zero net charge (i.e. the "isoelectric pH"). For example: silica in the presence of a singly valent counterion (e.g. $Na^+$) displays an isoelectric pH of about 2.8. Whereas silica in the presence of a bivalent counterion (e.g. $Ca^{2+}$ or $Ba^{2+}$) displays an isoelectric pH in the range of 6 to 7. In this regard, the transport fluid preferably is selected or purified so as to be substantially free of polyvalent counterions.

Ionic additives to the fluid may be broken into two general classes: those that fully ionize (e.g. salts, strong acids and strong bases) and those that partially ionize. The former class is often employed primarily to establish the ionic strength of the fluid. The latter class is often employed primarily to buffer the fluid and thus establish and maintain the pH of the fluid. The two classes often are used in conjunction. It is important to note that many but not all buffering species can exist in polyvalent states (e.g. formate exists as neutral or singly charged whereas phosphate exists as neutral, singly, doubly and triply charged). Thus the choice of a buffering compound must be made in view of the issue of polyvalent counterions discussed above.

Examples of ionic and buffering additives include but are not limited to: alkali-halide salts, mineral acids and bases, organic acids and bases, phosphates, borates, acetates, citrates, malates, formates, carbonates, chlorates, nitrates, sulfates and sulfites, nitrates and nitrites, ammonium-, methylammonium-, ethylammonium-, propylammonium-salts, BIS, MES, TRIS, TES, HEPES, TEA.

Certain compounds (sometimes termed anti-static agents) are known to alter or eliminate the zeta potential. For example special agents are added to hydrocarbon fuels to eliminate zeta potentials and thus prevent static buildup during pumping and transport. As a further example, special agents are added to shampoos and conditioners again to eliminate the zeta potential and prevent static buildup. Certain surfactants represent one class of these agents. In this regard the transport fluid is selected or purified so as to be substantially free of agents that degrade or eliminate the zeta potential. As examples: addition of small quantities of the surfactant SDS (sodium dodecyl sulfate) is known to increase the zeta potential of silica in aqueous solutions. Whereas the effect of the surfactant CTAB (cetyl trimethylammonium bromide) on silica in water is to reduce the zeta potential upon addition at low concentrations, to a value near zero as the concentration is increased, and to reverse the sign of the zeta potential at even higher concentrations. Addition of polyamines are also known to reduce or reverse the zeta potential of silica. Surface modification properties of surfactants are reviewed by M. J. Rosen, 'Adsorption of surface-active agents at interfaces: the electrical double layer,' Chapter II in, *Surfactants and Interaction Phenomena* (Wiley, N.Y., 1986), pp. 33-107.

The region of net charge in the fluid and adjacent to the dielectric surface extends some distance into the fluid. The one-on-e (1/e) thickness of this layer is approximately the Debye length in the bulk fluid. The Debye length at a temperature of 20° C. has a value of 0.048 nm times the square root of ratio of the fluid dielectric constant to the fluid ionic strength (the later taken in units of mols/liter). For one millimolar KCl in water the Debye length is about 9.6 nm.

This Debye length scale can be altered by changing the ionic strength of the fluid and is preferably less than about one-fifth the characteristic pore size of the porous dielectric medium. For Debye lengths greater than about one-fifth the characteristic pore size, the charged layers on opposing walls of the pore begin to substantially merge having the effect of reducing the apparent zeta potential. For quantitative determination of the degree of double layer overlap the characteristic pore size, $D_{pore}$, is preferably taken as defined by D. L. Johnson and P. N. Sen, Phys. Rev. B 37, 3502-3510 (1988); D. L. Johnson, J. Koplick and J. M. Schwartz, Phys. Rev. Lett. 57, 2564-2567 (1986); and D. L. Johnson, J. Koplick and R. Dashen, J. Fluid Mech. 176, 379-392 (1987). This definition of $D_{pore}$ produces a strong weighting in favor of the larger through-pores in a porous medium.

The flowrate through a porous medium is given by Darcy's law:

$$Q=-k_D \Delta P A/L$$

Here $\Delta P$ is the applied pressure difference driving the flow, A and L are the geometrical cross sectional area and thickness of the porous medium, respectively, $k_D$ is the flow or Darcy permeability of the medium. Using the definition of $D_{pore}$ given above, the Darcy permeability is given by:

$$k_D=D_{pore}^2 M/F$$

where M is termed the 'pore geometry number' and F is the 'formation factor' of the porous media. The formation factor, F, may be related to more common descriptors of porous media via $F=\tau^2/\phi$ where $\tau$ is termed the tortuoisty and $\phi$ is the connected porosity of the solid. The connected porosity is the wetted volume fraction that represents the through-connected pores and excludes dead-ended pores. Each of these descriptors may be determined using any of the methods well known in the art.

The effect of charge-layer overlap in simple geometries (e.g. slit or circular pores) has been studied theoretically. See, e.g., C. L. Rice and R. Whitehead, 'Electrokinetic flow in a narrow cylindrical pore,' J. Phys. Chem. 69 pp. 4017-4024 (1965); and D. Burgreen and F. R. Nakache 'Electrokinetic flow in ultrafine capillary slit,' J. Phys. Chem. 68 pp. 1084-1091 (1964). The conclusions of these studies can be applied analogously to a general porous medium through the use of $D_{pore}$ as defined above.

Pores in a porous material vary in size along the length and a variety of pore sizes may be present. Thus a general porous material, saturated with a fluid at some given ionic strength, may have some subset of pores that contain substantially overlapped regions of net charge (here termed 'nanopores') with the balance of the pores containing some amount of core fluid that is free of charge-layer overlap (here termed 'regular' pores). All of the pores will transport current hence ionic species, but the nanopores will transport flow at a greatly reduced rate compared to the regular pores. An object of the present invention is to apply a current so as to create a flow with minimal alteration of fluid ionic composition. The presence of nanopores reduces the efficiency of this process and may also lead to substantial and performance-degrading ionic strength, composition, and pH gradients across the porous element.

Experimental and theoretical studies of a wide range of porous media suggest that the pore geometry number falls into the range $1/32<M<1/16$, whereas the formation factor, F, is simply greater than or equal to the inverse of the connected porosity. No particular conditions are placed on the values of M or F for practice of the present invention, except to the extent that both values remain finite (essentially a condition that the porous material is indeed porous and connected end-to-end). Note that the topology properties of a porous material are important design parameters and also that optimization of a particular design may involve the specific choice of porous materials having particular values for these parameters.

Porous materials may be fabricated by a wide variety of methods, examples include but are not limited to the following:

Packed particles where the particles may be glass or ceramic or polymers. The particles may be held in place (i.e. confined in the channel) by any method known in the art, including but not limited to end-frits or other mechanical restrictions, or by cold welding under pressure or chemical bonding.

Synthetic porous opaline materials, such as those described in, for example, A. P. Philipse, 'Solid opaline packings of colloidal silica spheres,' J. Mat. Sci. Lett. 8 pp. 1371-1373 (1989), and porous materials created by using opalines as a template, as described in, for example, J. E. G. J. Wijnhoven and W. L. Vos, 'Preparation of photonic crystals made of air spheres in titania,' Science 281 pp. 802-804 (1998).

Phase separation and chemical leaching of a glass, for example the Vycor process as applied to a borosilicate or other composite glass as described in, for example, T. Yazawa, 'Present status and future potential of preparation of porous glass and its application,' Key Engineering Materials,' 115 pp. 125-146 (1996).

Solgel or aerogel process in silica, alumina, titania, zirconia and other inorganic-oxides or mixtures thereof.

Zeolite and zeolite-like porous media as described in, for example, Y. Ma, W. Tong, H. Zhou, S. L. Suib, 'A review of zeolite-like porous materials,' Microporous and Mesoporous Materials 37 pp. 243-252 (2000).

Phase separation of polymer—inorganic oxide solutions as carried out using, for example the SilicaRod process described in, for example, K. Nakanishi and N. Soga, 'Phase separation in silica sol-gel system containing polyacrylic acid I. Gel formation behavior and effect of solvent composition,' J. Non-crystalline Solids 139 pp. 1-13 (1992).

Direct machining by lithography and etching, molding, casting, laser ablation and other methods known in the arts.

Porous polymers as prepared by film stretching, sintering, track etching, casting followed by leaching or evaporation, slip casting, phase inversion, thermal phase inversion. Like methods are often employed in the manufacture of polymer filter membranes.

Porous polymer monoliths as described in, for example, E. C. Peters, M. Petro, F. Svec and J. M. Frechet, 'Molded rigid polymer monoliths as separation media for capillary electrochromatography,' Anal. Chem. 69 pp. 3646-3649 (1997).

Anodic etching as applied to silicon, as described in, for example, J. Drott, K. Lindstrom, L. Rosengren and T. Laurell, 'Porous silicon as the carrier matrix in micro structured enzyme reactors yielding high enzyme activities,' J. Micromech. Microeng. 7 pp 14-23 (1997) or as applied to aluminum as described in, for example, O. Jessensky, F. Muller and U. Gosele, 'Self-organized formation of hexagonal pore structure in anodic alumina,' J. Electrochem. Soc. 145 pp. 3735-3740 (1998).

The porous materials may be fabricated in-channel or may be fabricated, possibly machined or cut, and then inserted or sealed into the channel. The surface properties may be altered before or after placement within a channel.

The sign and magnitude of the zeta potential can be altered or enhanced by modification of the surface or bulk chemistry of the porous material as described above. Modification of surface chemistry is generally done by reaction with sites (e.g. silanol, hydroxyl, amine) that are present on the native material. Modification of the bulk chemistry is generally done by synthesis of a material that directly incorporates ionizable sites. Examples include but are not limited to the following:

Modification of the bulk chemistry of a polysulfone or polyethersulfone to convert some portion of the S=O groups to sulfonic acids. The sulfonic acid groups then providing a strongly acidic surface site.

Modification of the bulk chemistry of PTFE to attach side chains terminated in sulfonic acid groups (Dupont product Nafion™). The sulfonic acid groups then provide a strongly acidic surface site.

Modification of the bulk chemistry of a polyethersulfone or a polyvinyledene fluoride to introduce quaternary amines. The quaternary amine groups then provide a strongly basic surface site.

Modification of the bulk or surface chemistry of a polyamide (Nylon) to provide a material with only carboxy (acidic) or amine (basic) surface sites.

Modification of a zwitterionic material (e.g. Nylon) to terminate one of the existing ionizable sites with a non-ionizable end group. The material is then converted to one having only a basic or an acidic site, rather than one having both types.

Activation of a polymer material by introduction of defects or creation of cross-links via exposure to a plasma, ultraviolet or ionizing radiation. This creates reactive surface sites such as carboxyls.

Modification of surface silanol groups with methoxy- or chloro-silanes to create amino groups or sulfonic acid groups.

The porous dielectric material is contained in a fluid-impermeable 'channel' having a fluid inlet and outlet and spaced electrodes for applying a potential difference to the fluid. Channel materials are selected to meet requirements for mechanical strength, dielectric breakdown strength, transport fluid and fluid additive compatibility, and the capacity to retain the porous dielectric material. The geometry of the channel covers the entire range from long in length and small cross section to short in length and large cross section. An example of the former geometry is a channel that may be a capillary tube or a covered microchannel formed in a substrate having cross sectional shapes including round to rectangular to rectangular with sloped or curved sides. This channel may be formed by any of the means known in the art. An example of the later geometry is a large diameter and thin porous membrane as sandwiched between two electrodes The choice of pore size, topology numbers and physical geometry (e.g. porous element thickness and cross-sectional area) are particular to a given application. This then drives the needs for ionic strength and buffering capacity. In general, the following considerations may be taken into account for practicing preferred embodiments of the present invention.

Use of singly valent counterions for a well defined hence well-behaved zeta potential.

Use of absence of compounds in the fluid that degrade or eliminate the zeta potential.

Use of the lowest concentration of ionic species compatible with 'minimal' double layer overlap (i.e. a concentration yielding a fluid Debye length that is less than about one-fifth the characteristic pore size).

Use of the lowest concentration of buffering ionic species consistent with establishing and maintaining the pH of the fluid.

Use of ionic species that are compatible with, well soluble, and well dissociated in the fluid.

A pore size distribution that is preferably monodisperse and if polydisperse does not contain occasional large pores or defects (e.g. cracks or voids) and contains no or a minimal number of 'nanopores'

Use of a porous dielectric material that is less conducting than the fluid with additives.

Use of a porous dielectric material with a dielectric strength sufficient to withstand the potentials applied without dielectric breakdown.

Use of a porous dielectric material that is mechanically strong enough to withstand the pressures applied both as regards the ability to withstand compression and collapse, and the ability to remain attached to the material of the bounding channel.

Use of a porous dielectric material that is resistant and insoluble in the transport fluid with additives.

Use of a channel material that is an insulator, and in particular the channel material should be less conducting than the fluid with additives.

Use of a channel material with a dielectric strength sufficient to withstand the potentials applied without dielectric breakdown.

Use of a channel material that is mechanically strong enough and thick enough to withstand the pressures applied.

Use of a channel material that is resistant and insoluble in the transport fluid with additives.

Use of a fluid with a high value of the dielectric constant and a low value of the dynamic viscosity.

Use of a combination of fluid, surface chemistry and additive ionic species chemistry that provides a high value of the zeta potential.

Use of a fluid that is a pure fluid or a highly miscible mixture of pure fluids.

The principles and operation of the invention will now be described by reference to the following figures which are intended to serve as illustrative embodiments but not to limit the scope of the invention.

Figure 1A:
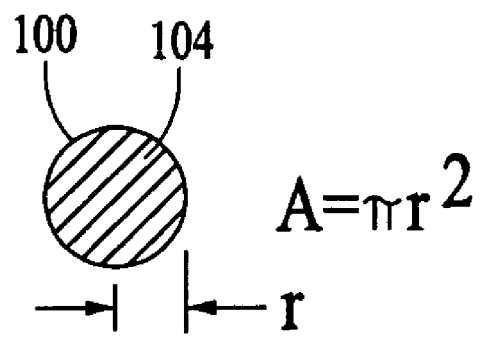
FIG. 1a illustrates a cross-section through a channel filled with a porous dielectric material.

FIG. 1 illustrates an "in-line" or "series type" flow controller embodiment of the invention. With respect to FIGS. 1 and 1a, consider a channel 100 of total cross-section A and of total length L that is packed with a porous dielectric medium 104. The channel 100 has an inlet 101 that is in fluid communication with a fluid source 102 at pressure P1 and an outlet 103 at pressure P2, where P2<P1. Throughout this description, we have assumed negligible resistance to fluid flow (and so negligible pressure drops) between the fluid source 102 and the inlet 101, and between the fluid outlet 103 and the fluid-collection reservoir 109. Under such circumstances, the pressure drop $\Delta P$ across channel 100 is equal to P2−P1. One of skill in the art readily will appreciate how to modify the equations below to account for pressure drops between the fluid source 102 and the inlet 101, and between the fluid outlet 103, and the fluid collection reservoir 109 by adjusting the term $\Delta P$ so that it accurately reflects the pressure drop across channel 100. The flow rate Q is produced by the combined action of a potential difference $\Delta V$ generated by power source 107, and applied to the fluid within the channel through spaced electrodes 105, 106, and a pressure difference $\Delta P$ between the channel inlet 101 and channel outlet 103.

It is well-known to one of skill in the art that application of an electrical potential to a fluid via electrodes 105, 106 in that fluid can generate a current through the fluid, and that gas will be generated at the electrodes 105, 106 via electrolysis of the fluid. It is further appreciated that gas generation within a closed fluid channel may be undesirable. Thus, as shown in FIG. 1, a bridge 108 may be used to connect electrodes 105, 106 in the fluid-filled reservoirs 102, 109 to the fluid in the channel 100. Such bridges are well-known in the art, and are described, for example, in C. Desiderio, S. Fanali and P. Bocek, 'A new electrode chamber for stable performance in capillary electrophoresis,' Electrophoresis 20, 525-528 (1999), and generally comprise a porous membrane or porous solid selected to have sufficiently small pores so as to minimize fluid flow through the bridge, while at the same time to provide for the transport of ions (i.e. to allow current flow). Typical bridge materials include Nafion™ (an ion-selective polymeric membrane) or porous Vycor™ (a phase-separated and etched porous glass having a pore size on the order of 5 nm).

The flow rate may be written as: $Q=(v\Delta V-\kappa\Delta P)A/LF$. This relation is a well known combination of Darcy's law for pressure driven flow and the Helmholtz-Smoluchowski relation as adapted for electroosmotic flow in porous media. Here $v$ is the effective electroosmotic mobility, $\kappa$ is the Darcy permeability of the porous media as divided by the dynamic viscosity of the liquid, and F is the above-described the formation factor. The effective mobility may be written as $v=\in\zeta(1-\xi)/\mu$ where $\in$ and $\mu$ are the dielectric permittivity and dynamic viscosity of the fluid, respectively, $\zeta$ is the zeta potential and $\xi$ is a factor that provides for the effect of overlapping net charge layers (i.e. a reduction of the apparent zeta potential under conditions that the thickness of the charge layers becomes on the order of the size of the pores in the media). The zeta potential, hence the electroosmotic mobility, may be signed positive or negative depending on the nature of the fluid and the dielectric material (e.g. for a porous dielectric material 104 composed of $TiO_2$ saturated with an aqueous solution, the zeta potential will have a positive sign at low pH and a negative sign at high pH and will be negligibly small at the material iso-electric point which for $TiO_2$ is at about pH 6.2).

The present invention employs a combination of pressure- and electroosmotically-driven flows in a channel 100 filled with a porous dielectric material 104. The applied potential preferably is selected to yield an electroosmotic flow in the same direction as the pressure-driven flow (e.g. for $TiO_2$ at high pH, hence a negative zeta potential hence a negative electroosmotic mobility, the potential would be applied with the negative terminal downstream with respect to direction of the pressure-driven flow). In this configuration the maximum flow rate through the channel 100 will be given by the flow rate equation above and only limited by the magnitude of the potential applied, whereas the minimum flow rate will be for purely pressure-driven flow, that is with $\Delta V=0$, hence $Q=-\kappa\Delta PA/LF$. Thus the combination of pressure- and electroosmotically-driven flow in a channel 100 filled with a porous dielectric material 104 provides a voltage-controlled means to vary the flow rate through that channel. In effect, flow control is provided by varying the degree of electroosmotic 'assist' to the pressure-driven flow through the channel. As is explained in greater detail with respect to other preferred embodiments described below, sensors may be used to monitor parameters such as pressure, flow rate, etc. at one or more points in the flow controller system. Signals arising from these sensors may be used in a sense and control or servo loop to maintain the signal within a predetermined range by adjusting the voltage outputted by the power supply in response to deviations between the signal and a predetermined set point.

Figure 2:
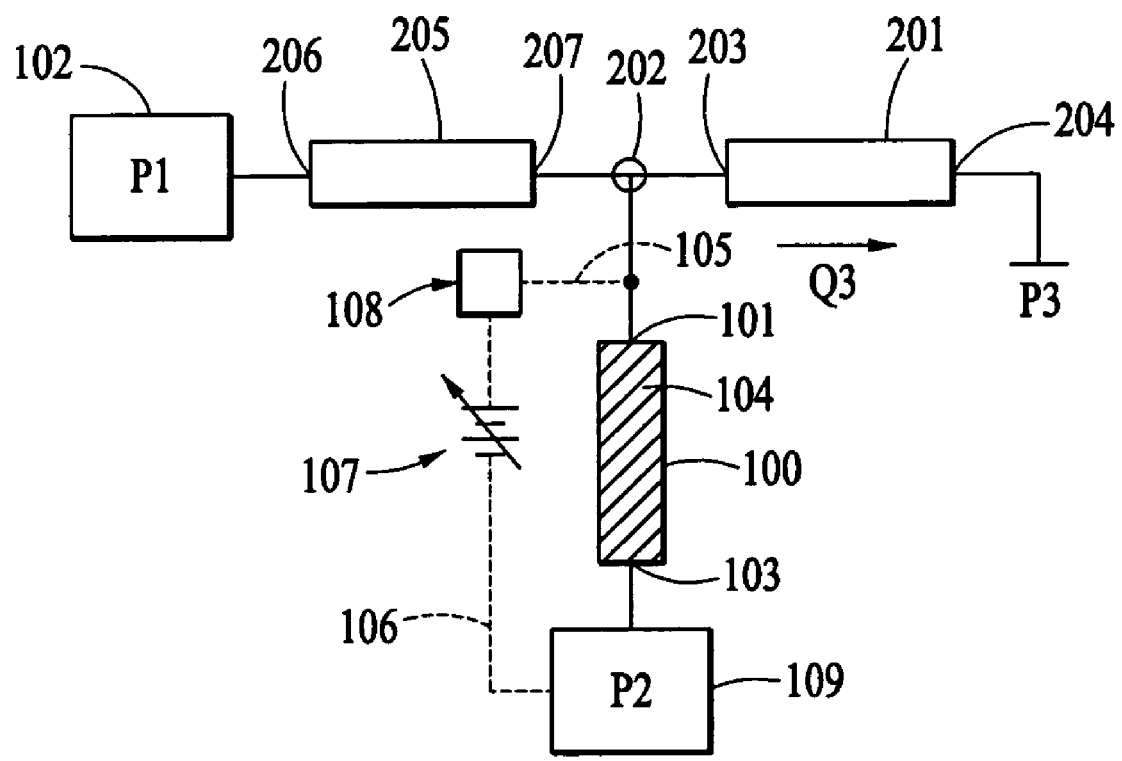
FIG. 2 illustrates a voltage-controlled flow splitter in accordance with an embodiment of the invention.

The system of FIG. 2 illustrates another preferred embodiment of the invention resulting in a device that acts as a voltage-controlled flow splitter. Fluid is supplied from a source 102 at a gauge pressure P1 and subsequently split at node 202 to flow through the device to a pair of fluid outlets 103, 204 at gauge pressures P2 and P3, respectively. The system of FIG. 2 may include flow element 205 with an inlet 206 that is in fluid communication with fluid source 102 at pressure P1 and an outlet 207 in fluid communication with node 202 at pressure $P_{node}$. Flow element 205 can be included to provide a pressure-driven flow resistance, or Darcy flow resistance, between the fluid source 102 at pressure P1 and node 202 so as to reduce the flow rate and pressure available at $P_{node}$ such that the maximum available pressure and maximum available flow rate established at node 202 is compatible with the electroosmotic flow rate of channel 100. This is accomplished by making the resistance of flow element 205 to be some fraction or multiple of the flow resistances of channel 100 and flow element 201.

Consider the gauge pressure P2 to be zero, that is, ambient pressure. However, this embodiment is not limited to this condition which is provided purely for illustration of this application. The flow rate $Q_3$ through flow element 201 is given by:

$$Q_3=k_3(k_1P_1(1-x)-(k_1+k_2)P_3)/(k_1+k_2+k_3)$$

Here we define the quantities: $k\equiv\kappa A/LF$ and $x\equiv(v_2/\kappa_2)k_2\Delta V/k_1P_1$. Those skilled in the art will note that the variable k can be considered effectively as the above-mentioned pressure-driven flow resistance parameter for each flow element or channel. Thus for $\Delta V=0$, hence $x=0$, the flow rate through flow element 201 has a value of:

$$Q_3=k_3(k_1P_1-(k_1+k_2)P_3)/(k_1+k_2+k_3)$$

whereas this flow rate $Q_3$ (i.e. the flow rate through flow element 201) is zero when:

$$x=1-(k_1+k_2)P_3/k_1P_1$$

hence this flow rate is zero when the potential is set to a value of $$\Delta V=(k_1P_1-(k_1+k_2)P_3)(\kappa_2/\nu_2)$$

The flow rate $Q_3$ through flow element 201 can be made negative (i.e. the flow direction through flow element reversed) by the application of even higher values of the potential.

The Darcy flow resistance for flow element 205 is selected based upon on the desired range of flow rates through flow element 201 and the electroosmotic flow rate that is achieved when a maximum voltage is supplied across channel 100 by power source 107. For example, if one desires the ability to halt flow through element 201, $P_{node}$ must be equal to P3. The pressure at node 202 is given by: $P_{node}=(k_1P_1(1-x)+k_3P_3)/(k_1+k_2+k_3)$. Thus, the relative resistances of flow element 205 and channel 100 should be designed to allow electroosmotic flow through channel 100 to be equal to the pressure driven flow through flow element 205. Appropriate selections of relative flow resistances for channel 100, flow element 205, and flow element 201 for a particular application are readily determined using the equations provided above by those skilled in the art.

Figure 3:
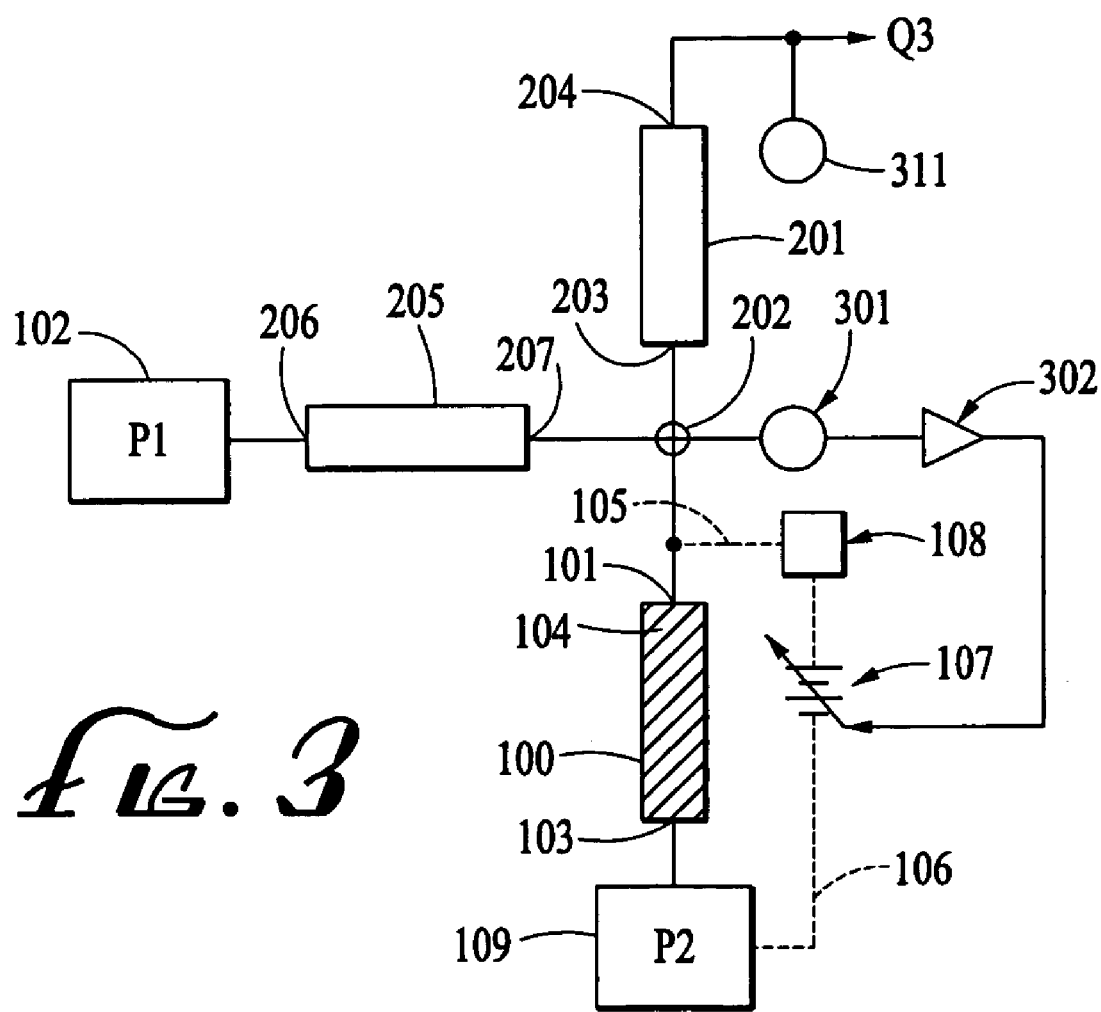
FIG. 3 illustrates an embodiment of the invention that includes a sensor and a servo loop controller for generating feedback signals and adjusting the power supply.

FIG. 3 illustrates an embodiment similar to that illustrated in FIG. 2, except for the addition of a sensor, 301, to monitor the pressure at the common node 202 of the flow elements shown in FIGS. 2 and 3. Sensor 301 can be employed along with servo loop controller 302 as part of a sense-and-control loop to regulate the pressure at the common node 202 and hence the flow rate, $Q_3$, through flow element 201. Flow rate $Q_3$ through flow element 201 also may be monitored directly or indirectly through sensor 311 as described in greater detail below. Such regulation may be desirable to compensate for variations in source pressure P1 (resulting, for example, from fluctuations in the output of a pump providing the pressure P1). Again referring to the example in which the gauge pressure P2 is zero (and again not limiting the invention to this particular condition), the flow rate $Q_3$ through flow element 201 is given by $Q_3=k_3(P_{node}-P_3)$ where the pressure at the node 202 is given by: $P_{node}=(k_1P_1(1-x)+k_3P_3)/(k_1+k_2+k_3)$. Thus variations in P1 can be compensated by adjustments to ΔV, hence x, so as to maintain a constant pressure at the node 202 and hence a particular flow rate $Q_3$ through flow element 201.

The control so achievable is limited by the condition that the pressure at P1 remains sufficiently high to supply the required flow rate. This type of feedback control may be accomplished by any of the means that are well-know in the art, for example: observing a pressure or flow reading at node 202 by use of sensor 301 and manually adjusting the potential applied by power source 107; measuring the pressure or flow at node 202 with sensor 301 and supplying this measurement to an analog electronic (or mechanical) servo loop controller 302 driving an electronically (or mechanically) adjustable power supply 107; measuring the pressure or flow at node 202 with a sensor 301 connected to a computer and using the computer to adjust power supply 107, optionally, with higher order corrections applied (e.g. corrections for fluid or sensor temperature variations) in light of other data being supplied to the computer.

One of skill will readily appreciate that multiple devices such as those illustrated in FIGS. 2 and 3, with or without servo-loop control, may be run in parallel to deliver multiple parallel sources of variable flow rate from one common source of fluid 102. The outlets of these parallel implementations need not but may terminate in loads at the same pressures. Similarly, the flow resistances and mobility coefficients of these parallel devices need not but may be the same.

The servo loop described above may employ a variety of control inputs and action outputs. By way of example, but not limitation, with the object of providing a constant flow rate $Q_3$ through flow element 201 the input to the servo loop is taken as, e.g., the differential pressure across flow element 201 (see FIG. 4, where sensors 301 and 311 may be used to measure pressure) or the differential pressure across some other passive pressure drop arranged in series with flow element 201. This differential pressure then provides a measure of the flow rate via Darcy's law. Alternatively the flow rate may be detected by other means know in the art, such as but not limited to: a turbine flowmeter, a thermal convection flowmeter, a Doppler flowmeter measured at or beyond fluid outlet 204.

Figure 4:
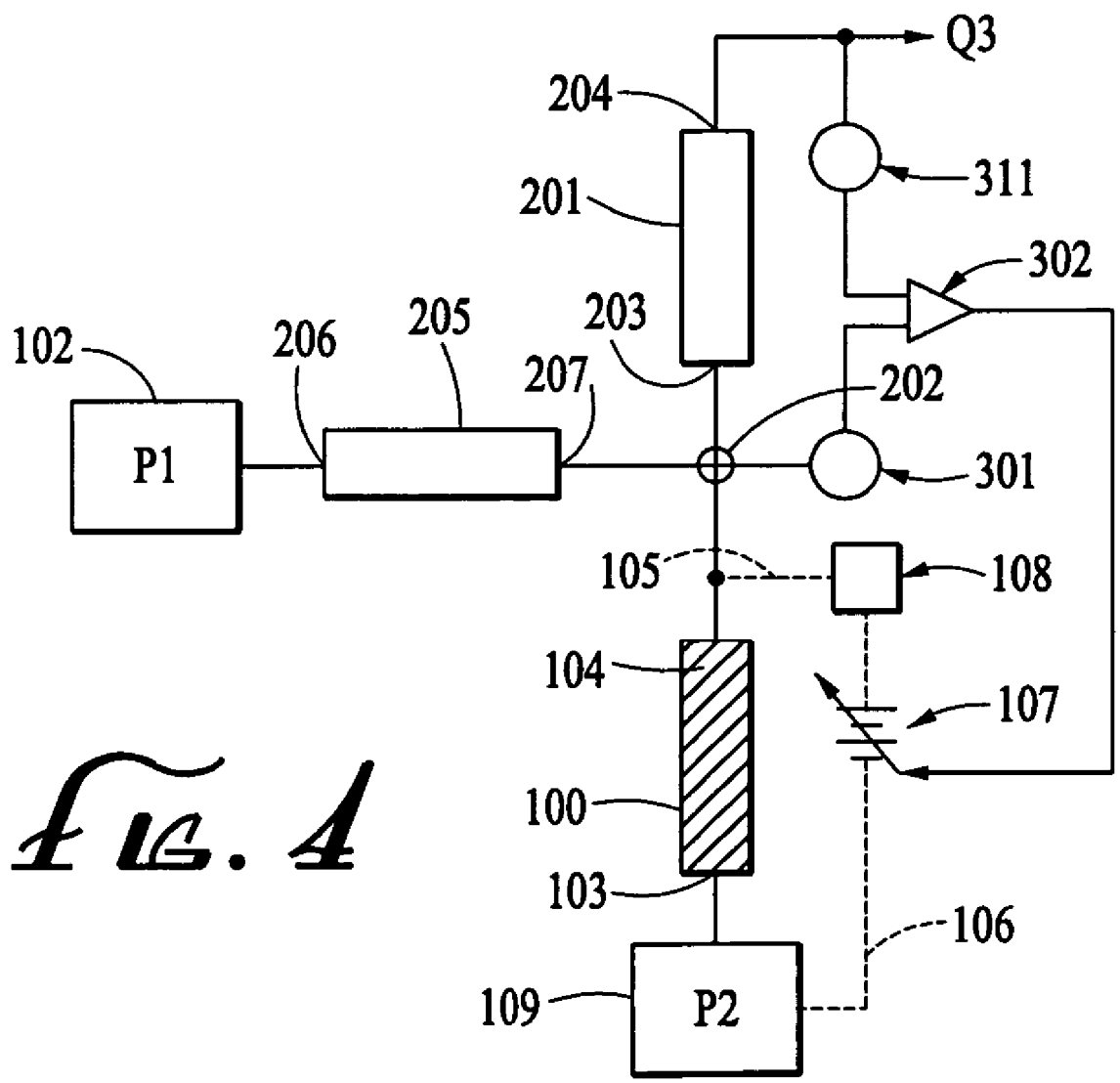
FIG. 4 illustrates an embodiment of the invention that includes two sensors and a servo loop controller for generating feedback signals and adjusting the power supply.

With the object to supply a flow rate of liquid used for heat transfer and by this the control of a temperature or heat flux as a result of the flow of liquid through flow element 201 sensors 301 and 311 (as shown in FIG. 4) may be used to measure temperature and flow element 201 is taken to be one side of a liquid heat exchanger or some further downstream element. For control of temperature the input to the servo loop may be a thermocouple or thermistor or RTD or other devices know in the art. For control of heat flux the input to the servo loop may be from a heat flux sensor or the temperature change of the fluid or other means know in the art.

Figure 5:
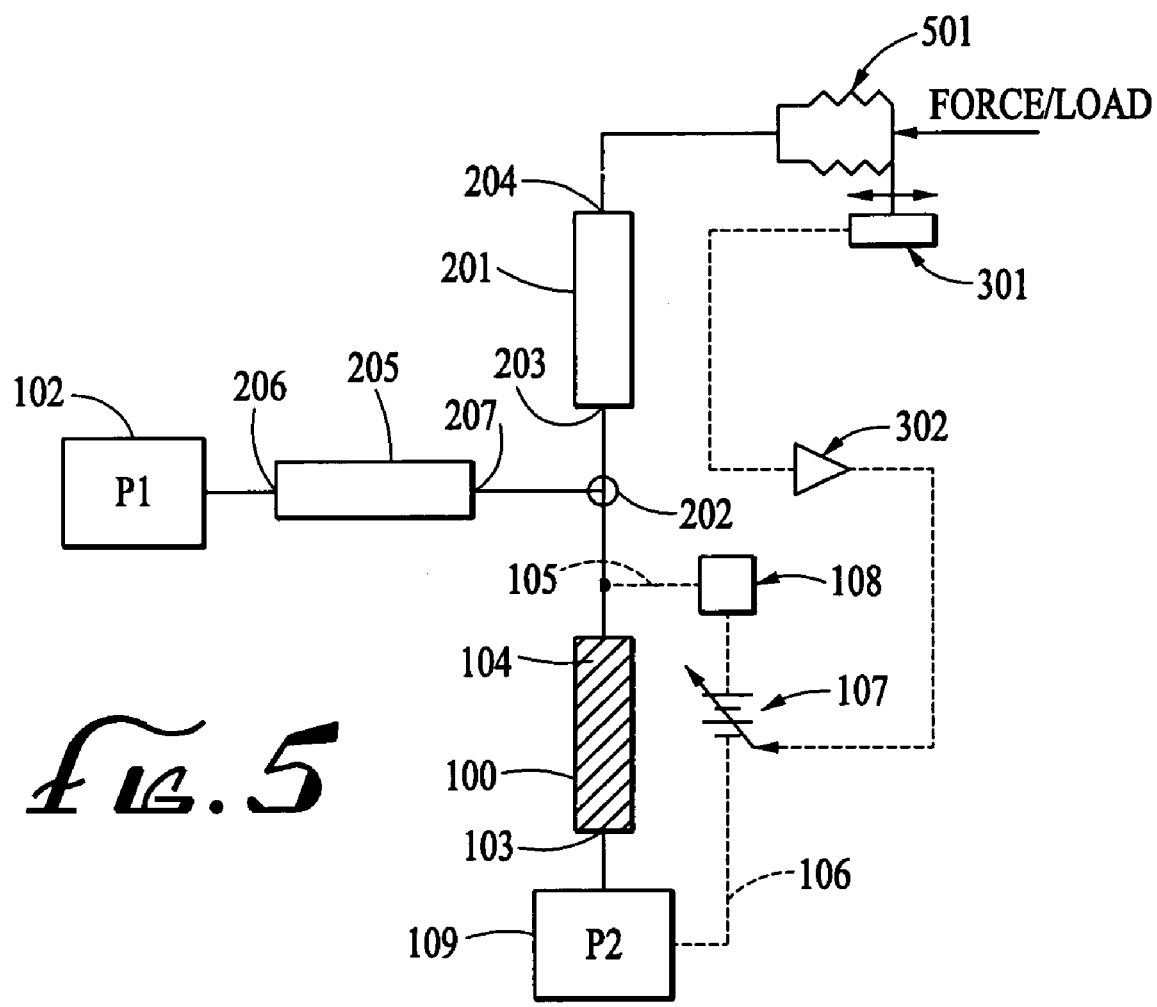
FIG. 5 illustrates an embodiment of the invention that includes a position or displacement sensor.

With the object of applying a mechanical force or displacement through the application of fluid pressure to a bellows 501 (see FIG. 5) or a piston or diaphragm or other means know in the art, the sensor 301 may be used to generate a signal for input to the servo loop from a load cell (for force) or a displacement sensor as know in the art. One of skill in the art readily will appreciate that hydraulic mechanical systems are preferably applied under compressive load conditions. For the case where the load is naturally compressive (e.g. gravitationally or spring return loaded) a single flow control system may be used to apply and control the hydraulic force acting against the load. For this case the potential applied by power supply 107 across channel 100 is reduced to increase flow towards the load thus pushing against the load, whereas the potential across channel 100 is increased to increase flow of fluid from the hydraulic actuator when the load is being returned. For the case where the load is neutral or where an active return force is required, two such flow control/servo systems may be used in a push-pull configuration.

The designs represented in FIGS. 1 through 5 illustrate several embodiments of the invention. It will be appreciated by those of skill in the art that these embodiments may be combined in a variety of series and parallel arrangements dictated by the problem or application at hand. In this regard, the embodiment illustrated in FIG. 1 may be considered as a form of in-line or series flow controller and the embodiments illustrated in FIGS. 2 through 5 may be considered forms of shunt or bleed flow controllers.

Figure 6:
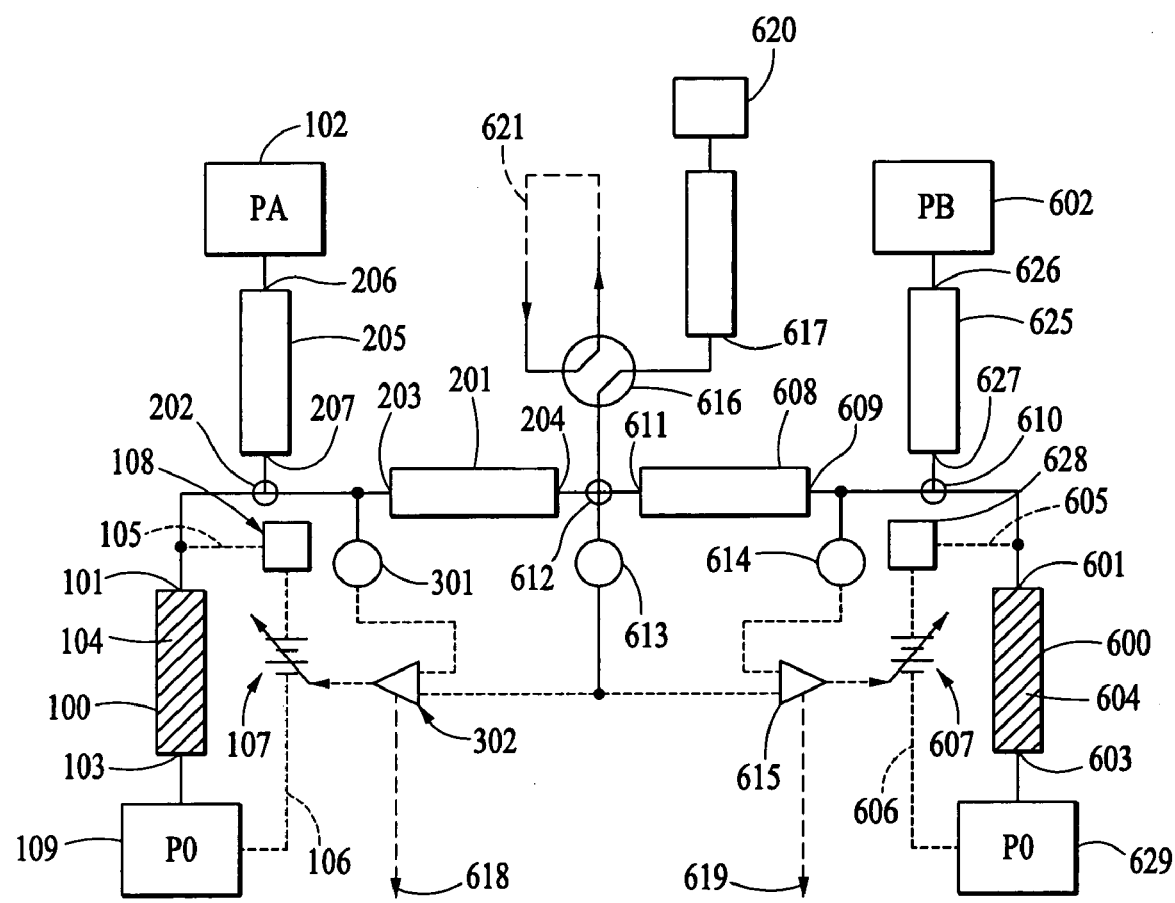
FIG. 6 illustrates an embodiment of the invention used to control the flow of two fluids. This embodiment can be used for generating fluid mixtures and gradients of the fluid mixtures for use in separations technologies.

The system illustrated in FIG. 6 shows a further embodiment of the invention useful for metering two fluids into a common stream. As one possible application and to illustrate this embodiment, such a system could be used to perform controlled mixing of two reagents or buffers to be used for gradient-type high pressure liquid chromatography (HPLC). As described above, the use of pressure sensing and servo-feedback control may be applied (as shown in FIG. 6) to monitor and/or control and/or regulate both the mixture and the output flow rate. Again this system and the invention is not limited to this particular example.

In the example of FIG. 6 sources of two fluids, A, and B, 102, 602, at gauge pressures PA and PB, are fed to two shunt-type controllers (having nodes 202, 610 and sensors 301, 614, monitoring node pressures P2A and P2B respectively) that feed fluid to a common junction 612 (at gauge pressure P3 monitored by sensor 613) where the fluids mix. This mixture is further supplied to sample injector 616 and then to a pressure-driven chromatographic column 617 (essentially a channel packed with porous media selected to provide different retention times for some set of chemical species). For purposes of this illustration, the outlet pressure of chromatography column 617 and of collection reservoirs 109, 629 for elements 100 and 600 are taken as ambient (however the invention is not restricted to these outlet pressures, nor by these outlet pressures being the same).

The objective in this illustration is to provide constant flow rate to the column 617 while providing a programmed variation in fluid composition. The flow rates of fluids A and B from sources 102 and 602 are independently measured and servo-controlled by two sense-and-control loops involving elements 301, 302, 107, 613, 614, 615, 607 that are provided with set-point inputs 618, 619. The programmed variation in fluid composition may be in the form of a series of step changes, or in the form of a continuous ramp (i.e. a gradient) or any of the other forms known in the separation arts. In applications requiring more than two sources of fluid, attendant flow controllers and servo loops may be combined to provide for more complicated or broad ranging fluid composition variations. Such configurations can be run in parallel from common sources of fluids to be able to perform multiple separations in parallel.

For the purpose of this illustration, sample injection through a sample loop 626 connected to a sample injector valve 616 at the head of the separation column 617 is taken to be performed by any of the means known in the HPLC arts (e.g. by a specialized sample injection valve e.g. 616, or by electroosmotic/electrophoretic injection through a porous media). For the purpose of this illustration, the end-use of the separation is taken to be any of the end-uses know in the HPLC arts (e.g. such as analyte detection by a detector 620 that measures, e.g., laser-induced fluorescence, optical absorption, refractive index or electrochemical potential; collection of the separation components; input to a mass spectrometer or ICP or NMR spectrometers; input to a next stage of separation by HPLC or LC or electrochromatographies; or preparative HPLC).

Figure 7:
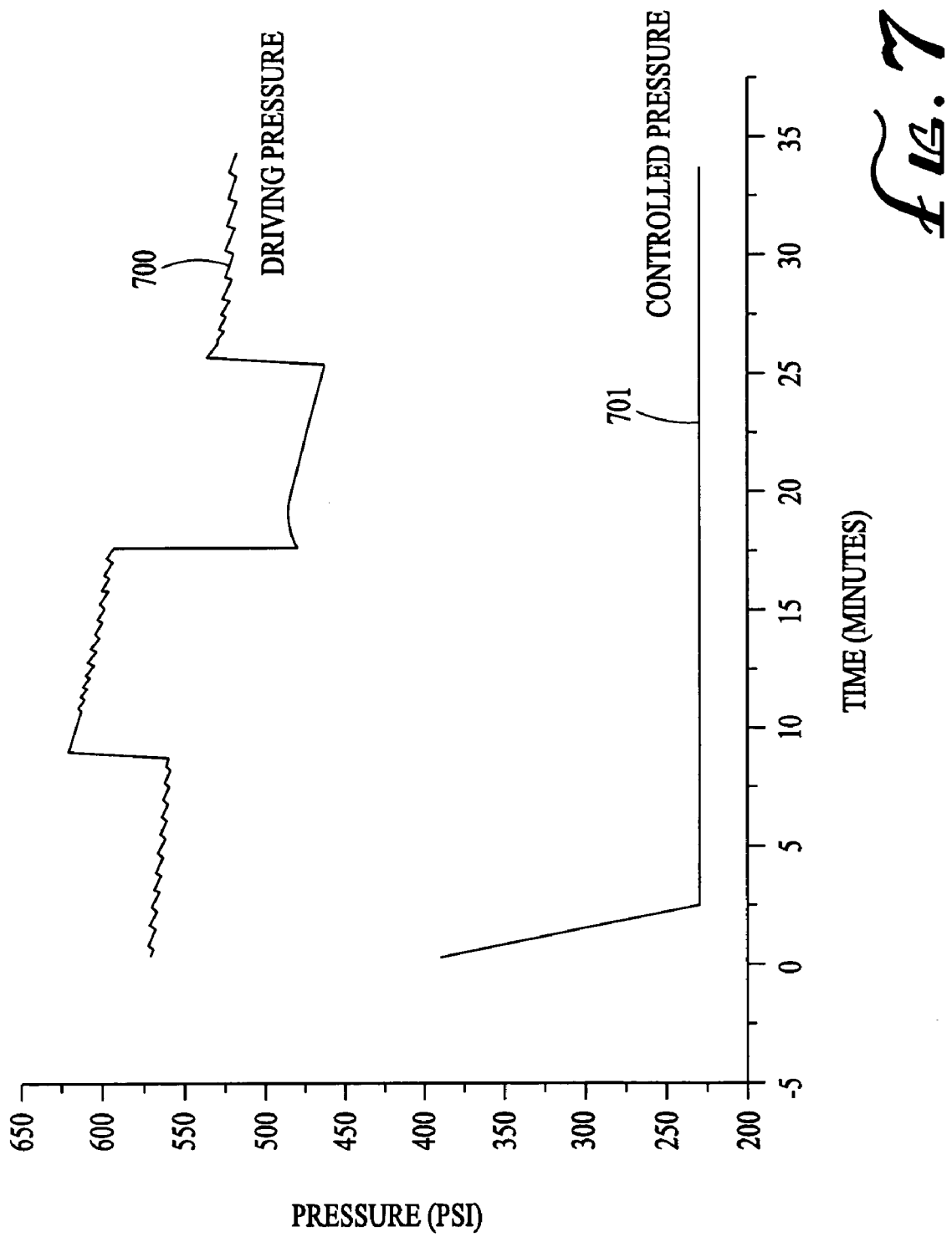
FIG. 7 illustrates controlled pressure generated by a flow controller of the invention despite varying driving pressure.
Figure 8:
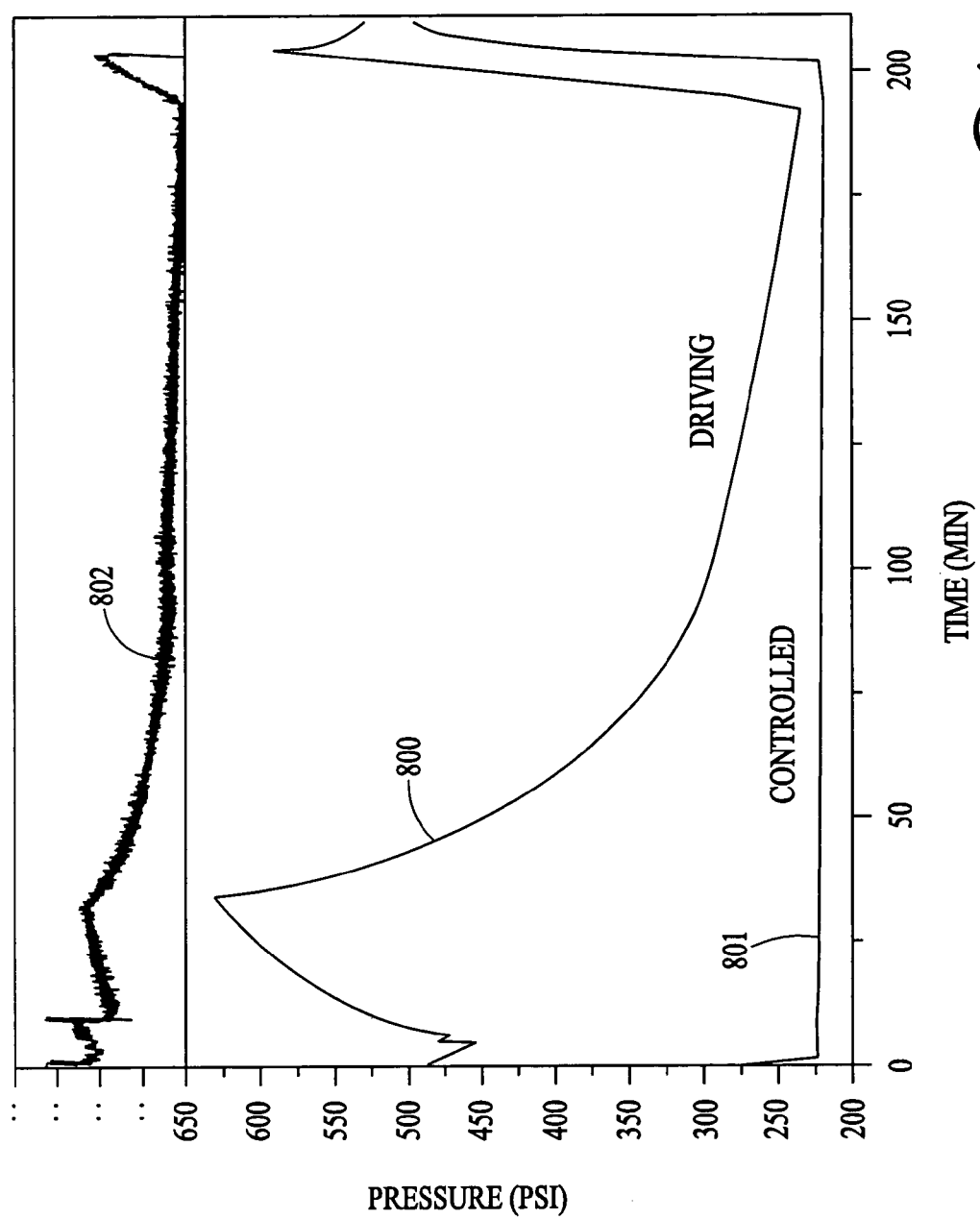
FIG. 8 illustrates controlled pressure generated by a flow controller of the invention despite decay in driving pressure.

FIGS. 7 and 8 show examples of flow control using the shunt-type flow controller configuration shown in FIG. 3. The flow elements were constructed from a section of 150 mm inner diameter silica capillary packed with 0.6 mm diameter non-porous silica beads. The flow elements, pressure transducers and pressure source were connected using conventional miniature HPLC fittings.

The data shown in FIG. 7 were generated using a commercial "lead-screw" type syringe pump as the pressure source (the ripples on the driving pressure curve (line 700) correspond to the well-known pressure fluctuations produced by a syringe pump). A time t=0 the controller was switched on with a set-point of ca. 225 psi. By t≈2.5 minutes the set point was achieved as illustrated by controlled pressure trace 701. Over the remainder of the test the feed rate of the syringe pump was changed several times, resulting in changes in the driving pressure 700 but the changes in the driving pressure 700 produced less than 2% variation in the controlled pressure 701. The driving pressure oscillations apparent in trace 700 were effectively removed by the flow controller, and so are absent in the controlled pressure trace 701.

The data shown in FIG. 8 also were generated using a commercial "lead-screw" type syringe pump. Again at t=0 the controller was switched on and the controlled pressure 801 set point of ca. 225 psi was quickly achieved. In this example the driving pressure 800 was increased and the syringe pump then was switched off resulting in decay of driving pressure 800 over a period of time. By ca. 190 minutes the driving pressure 800 had fallen to ca. 240 psi. whereas the controller maintained the controlled pressure set point of ca. 225 psi. Thus, flow control was achieved with a driving pressure only slightly greater than the set point pressure. The top trace 802 in FIG. 8 shows the current drawn through the flow control element.

Figure 9:
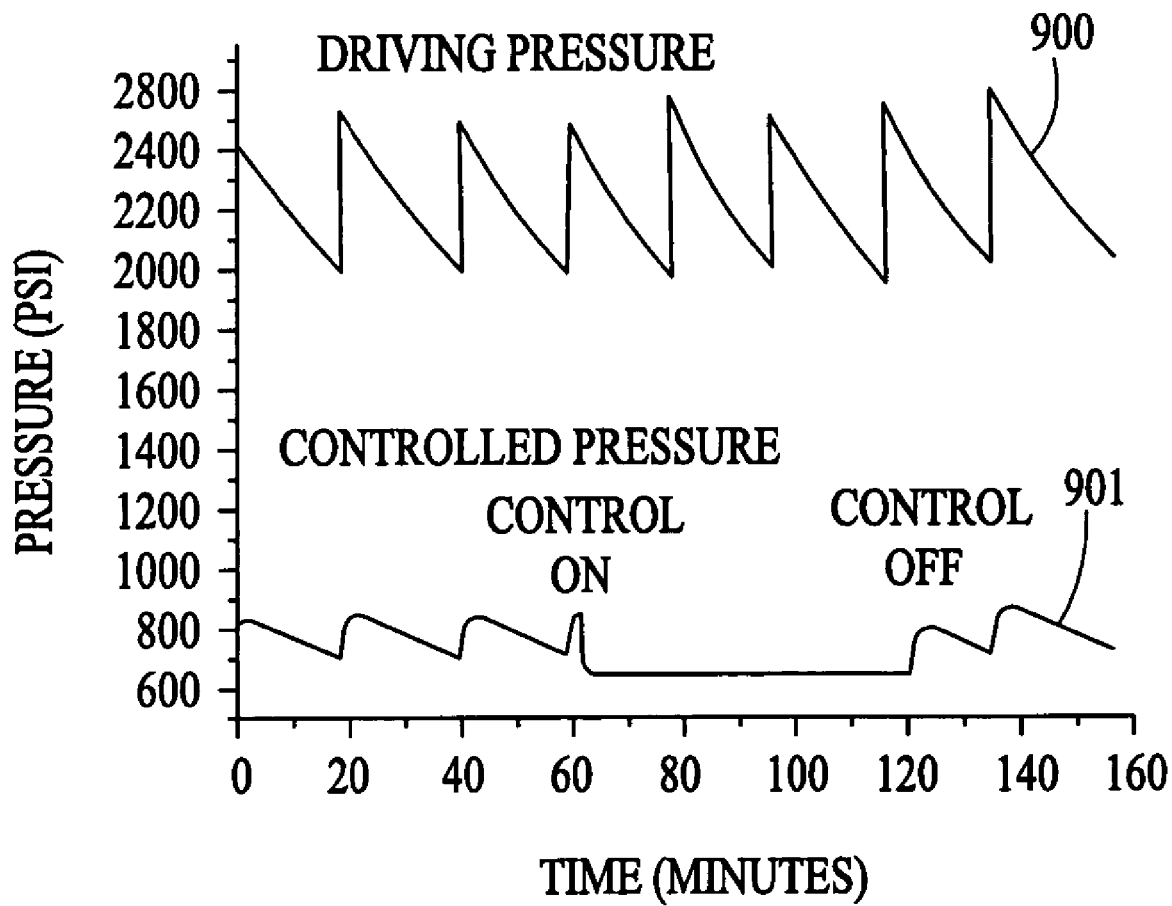
FIG. 9 is a graph showing driving pressure and column pressure as functions of time.

FIG. 9 shows pressure data from a nanobore capillary system driven by a traditional HPLC pump. The flow rate of the HPLC pump monitored by trace 900 showing pump output pressure is unstable in the microsystem causing 150 psi spikes monitored by a pressure transducer at the column head, the output of which is shown by trace 901. Switching on the flow controller (between approximately 60 and 120 minutes) allows the pressure and flow rate to the column to be precisely controlled. Over the range where the flow controller operates the root mean squared ("RMS") variation in pressure around the 650 psi set point is 1.7 psi. At the 8.5 nL/sec flow rate in the column, this correlates to a RMS variation in flow rate of 0.02 nL/sec.

Since the set point of the flow controller can be changed to almost any value less than the driving pressure, two or more flow controllers may be combined to deliver fast, accurate, and reproducible gradients for use in microscale separations. A single pressure source can be used to drive all of the different fluids used in the gradient. Since the flow controller is a microscale device, it is compatible with being operated in a multiple parallel configuration.

Figure 10:
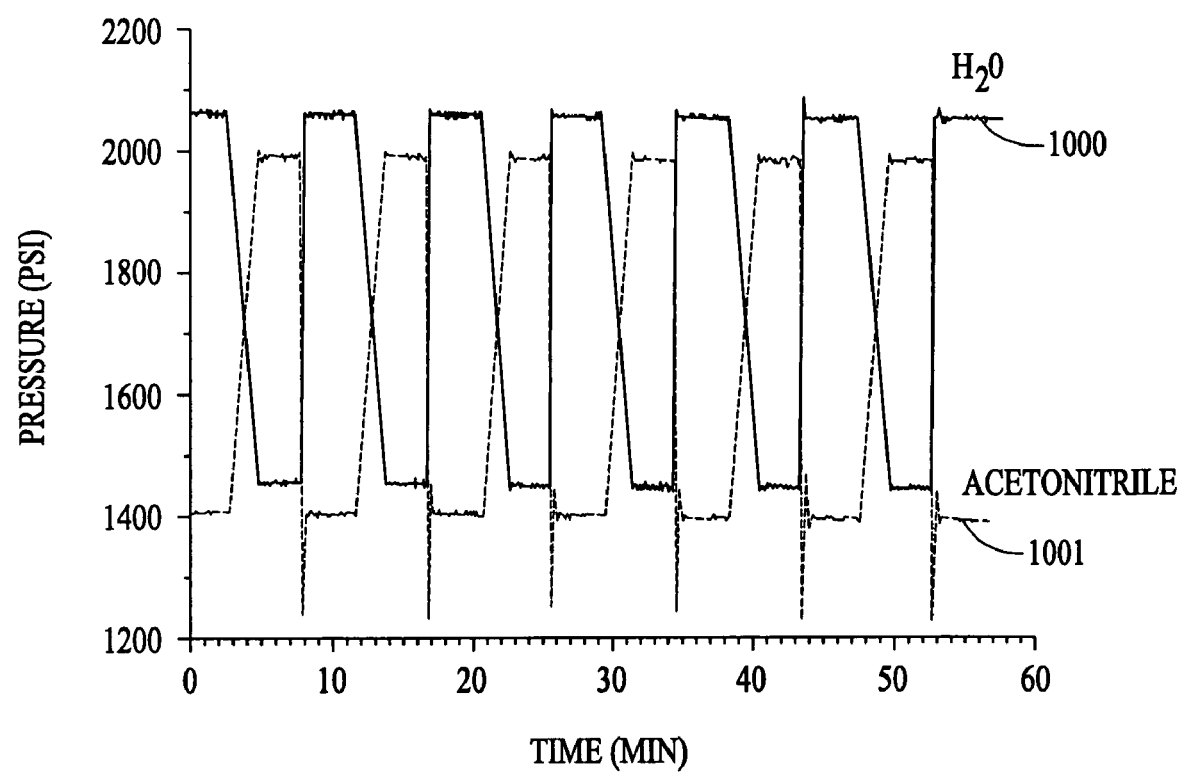
FIG. 10 is a graph showing reproducibility of water:acetonitrile gradients.

FIG. 10 shows the performance of a dual flow controller system such as the system illustrated in FIG. 6, programmed to generate water/acetonitrile gradients, illustrated in traces 1000 and 1001. The traces 1000 and 1001 correspond to pressures measured at nodes 202 and 610 illustrated in FIG. 6. Six gradients are repeated in the figure, starting at approximately 3, 12, 21, 30 and 39 minutes. The water and acetonitrile are both sloped several hundred psi from their starting to ending pressures over the 3 minute gradient and sent to a mixing tee at the head of the nanobore separation column. The gradient changes the composition of the mixed fluid while controlling the rate at which fluid is delivered to the nanobore separation column. The starting conditions of the gradient can be reestablished in less than 1 minute. In this system a simple hand-operated pump provides the driving pressure. The majority of the flow goes directly into the HPLC column; very little waste is produced. The flow rate in the separation column is compatible with feeding directly into a mass spectrometer. This demonstrates the ability of a dual flow controller system to quickly and reproducibly generate fast gradients in a nano bore HPLC system.

Figure 11:
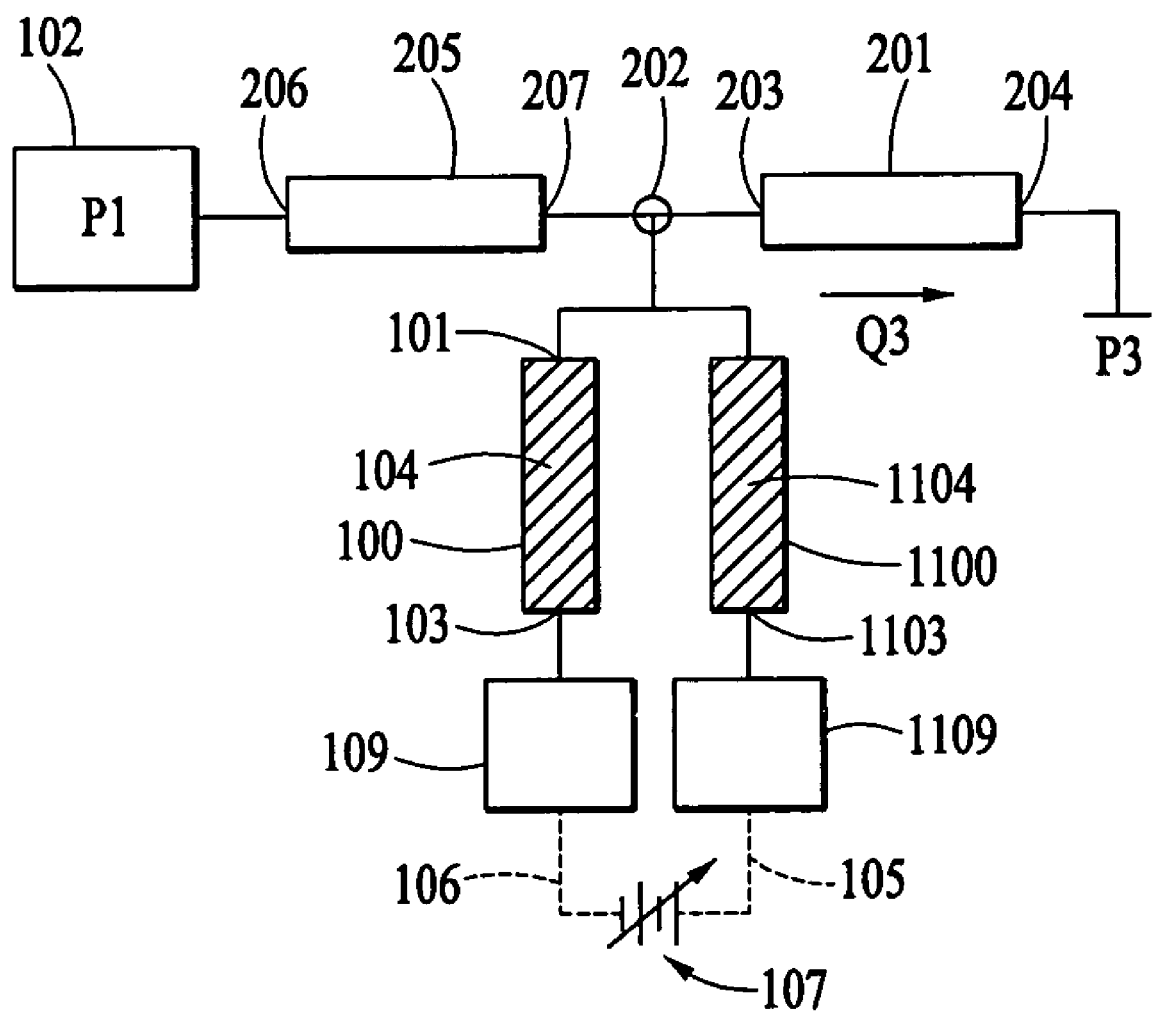
FIG. 11 illustrates an embodiment of the invention that provides a method to remove the electrode from the channel and an increased range of operating conditions.

As noted above, the presence of a current-carrying electrode in a closed channel may produce undesirable side effects. Bridges provide one method of removing the electrode from the channel but still providing current. As also noted above, the zeta potential is a function of fluid composition and pH. As such any given flow control porous element may operate under some limited range of fluid conditions. FIG. 11 shows an embodiment of the invention that provides both a method of removing the electrode from the closed channel and increasing the range of operating conditions. In FIG. 11 the flow control element channel 100 is replaced by two such channels in parallel 100 and 1100. The fluid outlets 103, 1103 of the two channels 100, 1100 are led into separate fluid reservoirs 109, 1109, both at the terminal pressure P2 that is less than source 102 pressure P1. Power from power supply 107 is supplied via electrodes 105, 106 in the these reservoirs. Current is then carried from power supply 107 through one channel (e.g. 100), back through the other channel (e.g. 1100) to the power supply 107. The common fluid connection of the channels (e.g., at node 202) may then be held at an arbitrary potential (preferably but not necessarily system ground). The channels 100 and 1100 comprise different zeta potential porous dielectric materials 104, 1104 having pore sizes sufficiently large to support electroosmotic flow. Note that this configuration reduces to the case of a bridge in the limit that one of the channels contains material having a pore size too small to support electroosmotic flow but large enough to still carry a current.

For example, the material 104 in channel 100 may be silica with a nominal iso-electric point of pH 3 and the material 1104 in channel 1100 may be alumina with an iso-electric point of pH 9.2. As a further example, the material 104 may be modified to display a sulfonic acid group (nominal iso-electric point of pH 1.5) and the media 1104 may be modified to support a quaternary amine (nominal iso-electric point higher than pH 14). For a fluid with a pH between the iso-electric points of the two materials the electroosmotic flow through one channel will be towards the supply anode and the electroosmotic flow through the other channel will be towards the supply cathode. This then provides flow hence flow control over a wider range of pH conditions than could be supported using a single channel and at the same time removes the current-carrying electrodes 105, 106 from the closed channels 100, 1100.

As a specific example consider the materials 104, 1104 in channels 100 and 1100 to be silica and alumina, respectively. With fluid having pH 3 channel 100 filled with silica has a negligible zeta potential and thus does not provide electroosmotic flow, but still carries current. Channel 1100 filled with alumina has a high positive zeta potential with fluid having pH 3 and thus provides the electroosmotic flow (from the common junction 202 of the channels towards the supply anode) needed for flow control. With fluid having pH 9 the roles are reversed, the silica displays a high negative zeta potential whereas the alumina has a negligible zeta potential, thus the electroosmotic flow is through channel 100 filled with silica (from the common junction 202 of the channels towards the supply cathode). For a fluid having a pH between pH 3 and pH 9 channels 100 and 1100 both supply some degree of electroosmotic flow and thus contribute to the ability to achieve flow control.

The foregoing description and figures are intended to illustrate but not limit the scope of the invention. Variations of what has been described will be apparent to those skilled in the art and are encompassed by invention described above. All references to patents, patent applications, and other publications are herein incorporated by reference in their entirety for any and all purposes.

What is claimed is:

1. A flow controller, comprising:
    (a) a channel having
        (i) a fluid inlet in liquid communication with a fluid source at pressure P1,
        (ii) a fluid outlet at pressure P2, wherein P2<P1, and
        (iii) a porous dielectric material disposed in said channel;
    (b) a fluid contained within said channel;
    (c) spaced electrodes in electrical communication with said fluid;
    (d) a power supply in electrical communication with said electrodes for applying an electric potential to said spaced electrodes;
    (e) a first node between the fluid inlet and the porous dielectric material;
    (f) a first flow element having a first flow element inlet in liquid communication at the first node at pressure PN with said fluid inlet and said fluid source, wherein P2<PN, and a first flow element outlet at pressure P3;
    (g) at least one sensor for monitoring at least one control signal; and
    (h) a feedback control mechanism operatively connected to the sensor and the power supply;
        whereby said electric potential generates an electroosmotically-driven flow component through said channel that modulates a pressure-driven flow component resulting from the P1–P2 pressure differential;
        whereby the electroosmotically driven flow component affects the proportion of fluid flowing through said channel and said first flow element; and
        whereby the feedback control mechanism maintains the at least one control signal within a predetermined range by modulating the electric potential applied by the power supply.

2. The flow controller of claim 1, further comprising:
    (f) a second flow element interposed between said fluid source and said first node, said second flow element having a second flow element inlet in liquid communication with said fluid source, and a second flow element outlet in liquid communication at said first node with said fluid inlet and said first flow element inlet.

3. The flow controller of claim 1, wherein said power supply is a variable power supply.

4. The flow controller of claim 1, wherein said pressure-driven and said electroosmotically-driven flow components through said channel are in the same direction.

5. The flow controller of claim 1, wherein said pressure-driven and said electroosmotically-driven flow components through said channel are in the opposite direction and the pressure-driven fluid flux is greater than or equal to the electroosmotically driven fluid flux.

6. The flow controller of claim 1, wherein said electrical communication is through a bridge.

7. The flow controller of claim 1, wherein said channel has a circular cross-section.

8. The flow controller of claim 1, wherein said channel comprises a fused silica capillary.

9. The flow controller of claim 1, wherein the porous dielectric material includes silica particles.

10. The flow controller of claim 9, wherein the silica particles have a diameter of between about 100 nm and 5 µm.

11. The flow controller of claim 1, wherein the porous dielectric material includes porous dielectric materials fabricated by processes selected from the group consisting of lithographic patterning and etching, direct injection molding, sol-gel processing, and electroforming.

12. The flow controller of claim 1, wherein the porous dielectric material includes organic polymer materials.

13. The flow controller of claim 1, wherein said at least one sensor is selected from the group consisting of a pressure transducer, a flowmeter, a temperature sensor, a heat flux sensor, a displacement sensor, a load cell, a strain gauge, a conductivity sensor, a selective ion sensor, a pH sensor, a flow spectrophotometer, and a turbidity sensor.

14. The flow controller of claim 13, wherein said at least one sensor is a pressure transducer.

15. The flow controller of claim 14, wherein said pressure transducer is a differential pressure transducer.

16. The flow controller of claim 13, wherein said at least one sensor is a flowmeter.

* * * * *